United States Patent
Tavares et al.

(10) Patent No.: US 7,018,649 B2
(45) Date of Patent: Mar. 28, 2006

(54) FELODIPINE TRANSDERMAL DEVICE AND METHODS

(75) Inventors: Lino Tavares, Kinnelon, NJ (US); Ihor Shevchuk, Yonkers, NY (US); Mark Alfonso, Easton, CT (US); Geraldine Marcenyac, Norwalk, CT (US); Kirti Valia, Plainsboro, NJ (US)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 10/045,595

(22) Filed: Oct. 23, 2001

(65) Prior Publication Data

US 2003/0072791 A1    Apr. 17, 2003

Related U.S. Application Data

(60) Provisional application No. 60/242,514, filed on Oct. 23, 2000.

(51) Int. Cl.
*A61F 13/00* (2006.01)
*A61F 13/02* (2006.01)
*A61L 15/16* (2006.01)

(52) U.S. Cl. .................. 424/449; 424/448
(58) Field of Classification Search ........... 424/449, 424/443, 448
See application file for complete search history.

(56) References Cited

U.S. PATENT DOCUMENTS

| | | | |
|---|---|---|---|
| 5,045,319 A * | 9/1991 | Chien et al. | 424/448 |
| 5,091,186 A * | 2/1992 | Miranda et al. | 424/448 |
| 5,225,199 A | 7/1993 | Hidaka et al. | 424/443 |
| 5,240,711 A | 8/1993 | Hille et al. | 424/448 |
| 5,834,496 A | 11/1998 | Young | 514/356 |
| 5,879,701 A | 3/1999 | Audett et al. | 424/448 |
| 5,968,547 A | 10/1999 | Reder et al. | 424/449 |
| 6,103,735 A | 8/2000 | Aslanian et al. | 514/290 |
| 6,541,479 B1 * | 4/2003 | Mehanna et al. | 514/255.01 |
| 2003/0199492 A1 * | 10/2003 | Scott | 514/211.07 |

FOREIGN PATENT DOCUMENTS

| | | |
|---|---|---|
| WO | 9310781 | 6/1993 |
| WO | 9619975 | 12/1995 |
| WO | 9637231 | 11/1996 |
| WO | 9836728 | 8/1998 |
| WO | 0045797 | 8/2000 |

OTHER PUBLICATIONS

Diez, I., et al., "Influence of d-limonene on the Transdermat Oenetration of Felodipine", European J. of Metab and Pharm., 1998 vol. 23 (1) pp 7-12.

* cited by examiner

*Primary Examiner*—Thurman K. Page
*Assistant Examiner*—Isis Ghali
(74) *Attorney, Agent, or Firm*—Davidson Davidson and Kappel, LLC

(57) ABSTRACT

A method of effectively treating hypertension in humans is achieved by administering felodipine via a transdermal formulation. Preferably, the transdermal formulation is applied to the skin of the patient and maintained in contact with the skin for at least about 24 hours days, and preferably for about 3 to about 8 days.

37 Claims, 16 Drawing Sheets

FELODIPINE TRANSDERMAL DEVICE AND METHODS

This application claims the benefit of U.S. Provisional Application No. 60/242,514, Filed Oct. 23, 2000, which is hereby incorporated by reference.

BACKGROUND OF THE INVENTION

It is the intent of all sustained-release pharmaceutical preparations to provide a longer period of pharmacologic effect after the administration of a drug than is ordinarily experienced after the administration of immediate release preparations of the same drug. Such longer periods of efficacy can provide many inherent therapeutic benefits that are not achieved with corresponding immediate release preparations. The benefits of prolonged treatment of hypertension (high blood pressure) afforded by sustained release oral preparations have become universally recognized and oral sustained-release preparations are commercially available.

Another approach to sustained delivery of a therapeutically active agent is transdermal delivery systems, such as transdermal patches. Generally, transdermal patches contain a therapeutically active agent, a reservoir or matrix containing the active ingredient(s) and an adhesive which allows the transdermal device to adhere to the skin, allowing for the passage of the active agent from the device through the skin of the patient. Once the active agent has penetrated the skin layer, the drug is absorbed into the blood stream where it can exert a desired pharmacotherapeutic effect.

Transdermal delivery of antihypertensives, such as felodipine, have been contemplated. For example, U.S. Pat. No. 5,834,496 issued Nov. 10, 1998 to Young, hereby incorporated by reference, relates to methods and compositions utilizing the optical pure (—S) isomer of felodipine for treating conditions such as hypertension, angina, cerebral ischemia, cerebral disorders, arrhythmias, cardiac hypertrophy, coronary vasospasm, myocardial infarction, renal impairment and acute renal failure.

Felodipine, commercially available as Plendil® in the U.S. from AstraZeneca Pharmaceuticals LP (Wilmington, Del. 15437, U.S.A.), is a calcium antagonist (calcium channel blocker). Specifically, felopine is a dihydropyridine derivative with the chemical name, 4-(2,3-dichlorophenyl)-1,4-dihydro-2,6-dimethyl-3,5-pyridinedicarboxylate, and it is used in the treatment of hypertension. It is a racemic mixture, and it is in the form of a slightly yellowish powder that is not soluble in water but freely soluble in dichloromethane and ethanol. Felodipine causes a decrease in the intracellular concentration of calcium ions, which leads to a reduction in blood pressure. The recommended starting oral dosage of felodipine is 5 mg once daily, and depending on the response of the patient can be increased up to 10 mg daily or decreased to 2.5 mg daily. In elderly patients or patients with liver or renal problems, the initial oral dosage felodopine should be 2.5 mg daily with the dosage being adjustable as set forth above.

High blood pressure or hypertension occurs when the blood exerts excessive force upon the walls of the arteries. Blood pressure is measured as two numbers; systolic (pressure of the blood in the arteries when the heart beats) and diastolic (pressure when the heart is at rest between heartbeats). A normal blood pressure is consider to be around 120 (systolic)/80 (diastolic) mm Hg, whereas a reading of about 140 (systolic)/90 (diastolic) mm Hg or higher is considered to be high blood pressure. High blood pressure causes the heart to work extra hard, which in turn eventually leads to an enlarged heart, putting the individual at increased risk of having a heart attack or stroke. Some possible causes of high blood pressure include thinning of the arteries, increased heart rate, increased volume of blood, excitement, and nervousness.

Symptoms of hypertension are improved by treatment with a group of antihypertensives known as calcium channel antagonists (calcium channel blockers). Calcium channel antagonists such as felodipine (The Merck Index, $11^{th}$ Edition, Merck & Co., Inc., Rahway, N.J. U.S.A. 1989, hereby incorporated by reference) inhibit the influx of extracellular calcium across the membranes of the myocardial and vascular smooth muscle cells, causing the blood vessels to relax, and thereby reducing blood pressure. (Goodman and Gillmans, The Pharmacological Basis of Therapeutics, $9^{th}$ Edition, hereby incorporated by reference). Felodipine has a greater selectively for vascular smooth muscle than for cardiac muscle.

Following oral administration, felodipine is rapidly absorbed and undergoes extensive first pass metabolism, resulting in a bioavailibility of approximately 20 percent. Pharmacokinetic studies have revealed that the onset of antihypertensive activity occurs within 2–5 hours following administration of felodipine. Mean peak concentrations are reached in 2.5–5 hours after administration. The mean elimination half-life is roughly 11 to 16 hours. Metabolism of felodopine results in its excretion in the urine (70%) and the feces (10%). Felodipine is 99% plasma-protein bound.

The most common adverse side effects of felopidine are peripheral edema and headaches. Other side effects include chest infection, dizziness, palpitations, diarrhea, constipation, flushing, rash, fatigue, and gingival enlargement (Physicians' Desk Reference, 53rd Edition, 1999, hereby incorporated by reference).

Despite advances in the art, there remains a need for methods of treating patients with hypertension with an agent that provides effective levels of felodipine for prolonged periods of time while eliminating or minimizing the symptoms of hypertension, and the above mentioned side effects, thus providing a safe and effective method of management of this condition.

OBJECTS AND SUMMARY OF THE INVENTION

It is an object of the present invention to provide a continuous plasma felodipine concentration in mammals, preferably human patients suffering from hypertension.

It is an object of the present invention to provide a method for treating patients suffering from hypertension with a transdermal delivery system, which achieves prolonged and effective management of this condition, while at the same time provides the opportunity to reduce possible side effects, e.g., which patients may experience when subjected to prolonged oral therapy.

It is another object to provide a method for the treatment of hypertension in patients by utilizing a transdermal delivery system, which contains felodipine.

In certain embodiments, the present invention is directed to a method of effectively treating hypertension, angina, or both conditions in a human patient, comprising administering felodipine transdermally to the human patient by applying a transdermal delivery system containing felodipine to the skin of a patient, and maintaining the transdermal delivery system in contact with the skin of the patient for at least 3 days, the transdermal delivery system maintaining an effective mean relative release rate to provide a therapeutic blood level of the felodipine within 36 hours from the initiation of the dosing interval, and thereafter maintaining a therapeutic blood level until the end of at least the three-day dosing interval.

In certain embodiments, the present invention is directed to a method of effectively treating hypertension, angina, or both conditions in a human patient, comprising administering felodipine transdermally to the human patient by applying a transdermal delivery system containing felodipine to the skin of a patient, and maintaining the transdermal delivery system in contact with the skin of the patient for at least 5 days, the transdermal delivery system maintaining an effective mean relative release rate to provide a therapeutic blood level of the felodipine within three days from the initiation of the dosing interval, and thereafter maintaining a therapeutic blood level until the end of at least the five-day dosing interval.

In certain embodiments, the present invention is directed to a method of lessening the incidence of side-effects in a patient associated with the oral administration of felodipine, wherein the method comprises administering the felodipine in a transdermal delivery system over at least twenty-four hours and thereby lessening the incidence of side effects.

In certain embodiments, the above methods can further comprise providing a mean relative release rate of felodipine from the transdermal delivery system to provide a plasma level of felodipine of at least about 0.1 ng/ml within about 6 hours, 3 hours, 2 hours, 1 hour or 0.5 hours after application of the transdermal delivery system onto the skin of the patient.

In certain embodiments, the above methods can further comprise providing a felodipine transdermal delivery system, which maintains a plasma level of felodipine at steady-state from about 1.0 to about 3.0 ng/ml or from about 1.5 to about 2.3 ng/ml.

In certain embodiments, the above methods can further comprise maintaining a therapeutic plasma level from about 0.1 ng/ml to about 3.3 ng/ml during the dosing interval for the transdermal delivery system.

In certain embodiments, the above methods can further comprise having the transdermal delivery system have a mean relative release rate from about 0.5 μm/hour/cm² to about 25 μm/hour/cm2, from about 1 μm/hour/cm² to about 20 μm/hour/cm², or from about 2 μm/hour/cm² to about 10 μm/hour/cm².

In certain embodiments, the above methods can further comprise having the transdermal delivery system have a mean relative release rate from about 4.2 μg/cm²/hr to about 20.0 μg/cm²/hr at 24 hours; from about 3.3 μg/cm²/hr to about 14.0 μg/cm²/hr at 48 hours; and from about 2.7 μg/cm²/hr to about 10.8 μg/cm²/hr at 72 hours; as determined via an in-vitro permeation test utilizing a Valia-Chien cell where the membrane is a human cadaver skin and the cell has a receptor chamber containing a 40:60 mixture of Ethanol:water.

In certain embodiments, the above methods can further comprise having the transdermal delivery system provide an in-vitro cumulative amount of permeation of from about 63 μg/cm² to about 388 μg/cm² at 24 hours; from about 105 μg/cm² to about 660 μg/cm² at 48 hours; and from about 139 μg/cm² to about 854 μg/cm² at 72 hours, as determined via an in-vitro permeation test utilizing a Valia-Chien cell where the membrane is a human cadaver skin and the cell has a receptor chamber containing a 40:60 mixture of Ethanol:water.

In certain embodiments, the above methods can further comprise having the plasma level of felodipine at 48 hours after administration not decrease by more than 30% over the next 72 hours.

In certain embodiments, the above methods can further comprise maintaining an effective mean relative release rate of the transdermal delivery system to provide a substantially first order plasma level increase of felodipine from the initiation of the dosing interval until about 48 to about 72 hours after the initiation of the dosing interval; and thereafter providing an effective mean relative release rate to provide a substantially zero order plasma level fluctuation of felodipine until the end of at least the five-day dosing interval.

In certain embodiments, the above methods can further comprise administering the felodipine in a transdermal delivery system applied to the skin of a human patient for about 3 to about 5 days.

In certain embodiments, the invention is directed to a transdermal delivery system containing felodipine or a pharmaceutically acceptable salt thereof which provides a mean relative release rate from about 0.5 μm/hour/cm² to about 25 μm/hour/cm², from about 1 μm/hour/cm² to about 20 μm/hour/cm², or from about 2 μm/hour/cm² to about 10 μm/hour/cm² of the transdermal delivery system; a plasma level of felodipine of at least about 0.1 ng/ml by about 6 hours after application of the transdermal delivery system onto the skin of the patient; and a plasma level of felodipine at steady-state from about 0.1 to about 3.3 ng/ml.

In certain embodiments, the invention is directed to a transdermal delivery system which provides a mean relative release rate from about 4.2 μg/cm²/hr to about 20.0 μg/cm²/hr at 24 hours; from about 3.3 μg/cm²/hr to about 14.0 μg/cm²/hr at 48 hours; and from about 2.7 μg/cm²/hr to about 10.8 μg/cm²/hr at 72 hours; as determined via an in-vitro permeation test utilizing a Valia-Chien cell where the membrane is a human cadaver skin and the cell has a receptor chamber containing a 40:60 mixture of Ethanol:water.

In certain embodiments, the invention is directed to a transdermal delivery system which provides an in-vitro cumulative amount of permeation of from about 63 μg/cm² to about 388 μg/cm² at 24 hours; from about 105 μg/cm² to about 660 μg/cm² at 48 hours; and from about 139 μg/cm² to about 854 μg/cm² at 72 hours; and from about 231 μg/cm² to about 850 μg/cm² at 96 hours; as determined via an in-vitro permeation test utilizing a Valia-Chien cell where the membrane is a human cadaver skin and the cell has a receptor chamber containing a 40:60 mixture of Ethanol:water.

In certain embodiments, the transdermal delivery system maintains a plasma level of felodipine at steady-state from about 1.0 to about 3.0 ng/ml or from about 1.5 to about 2.3 ng/ml.

In certain embodiments, the transdermal delivery system maintains an effective mean relative release rate to provide a therapeutic blood level of the felodipine within three days from the initiation of the dosing interval, and thereafter maintaining a therapeutic blood level until the end of at least the five-day dosing interval.

In certain embodiments, the transdermal delivery system provides a mean relative release rate of felodipine effective to provide a plasma level of felodipine of at least about 0.1 ng/ml by about 6 hours, 3 hours, 2 hours, 1 hour or 0.5 hours after application of the transdermal delivery system onto the skin of the patient.

In certain embodiments, the transdermal delivery system maintains a therapeutic plasma level from about 0.1 ng/ml to about 3.3 ng/ml during the dosing interval for the transdermal delivery system.

In certain embodiments, the transdermal delivery system provides a mean relative release rate from about 0.5 µg/hour/cm² to about 25 µg/hour/cm², from about 1 µm/hour/cm² to about 20 µm/hour/cm², or from about 2 µm/hour/cm² to about 10 µm/hour/cm² of the transdermal delivery system.

In certain embodiments, the transdermal delivery system provides a mean relative release rate from about 4.2 µg/cm²/hr to about 20.0 µg/cm²/hr at 24 hours; from about 3.3 µg/cm²/hr to about 14.0 µg/cm²/hr at 48 hours; and from about 2.7 µg/cm²/hr to about 10.8 µg/cm²/hr at 72 hours; and a mean relative release rate from about 2.4 µg/cm²/hr to about 8.9 µg/cm²/hr at 96 hours; as determined via an in-vitro permeation test utilizing a Valia-Chien cell where the membrane is a human cadaver skin and the cell has a receptor chamber containing a 40:60 mixture of Ethanol:water.

In certain embodiments, the transdermal delivery system provides an in-vitro cumulative amount of permeation of from about 63 µg/cm² to about 388 µg/cm² at 24 hours; from about 105 µg/cm² to about 660 µg/cm² at 48 hours; and from about 139 µg/cm² to about 854 µg/cm² at 72 hours; and from about 231 µg/cm² to about 850 µg/cm² at 96 hours; as determined via an in-vitro permeation test utilizing a Valia-Chien cell where the membrane is a human cadaver skin and the cell has a receptor chamber containing a 40:60 mixture of Ethanol:water.

It is another object to provide a transdermal device containing felodipine, which provides effective blood plasma levels of felodipine when the device is applied to the skin of a mammal, preferably a human.

It is another object of the invention to provide a transdermal device containing felodipine, which provides effective treatment of hypertension in patients.

It is yet a further object to provide a transdermal device containing felodipine and a method for the treatment of hypertension in patients which maximizes the dosage interval, i.e., the interval during which the transdermal delivery system is maintained in contact with the skin, and minimizes the plasma concentrations and or fluctuations in plasma concentrations in the patients during the dosage interval, while surprisingly maintaining effective management of hypertension.

It is yet a further object to provide transdermal delivery device comprising felodipine or a pharmaceutically acceptable salt thereof which maintains an effective mean relative release rate to provide a therapeutic blood level of the felodipine within three days from the initiation of the dosing interval, and thereafter maintaining a therapeutic blood level until the end of at least the five-day dosing interval.

It is yet a further object to provide a method for lessening the peripheral edema and headaches with the oral administration of felodipine.

In accordance with the above objects and others, the present invention is directed in part to a transdermal device for achieving the above methods.

In further embodiments, the invention is directed to a transdermal device and method which, when applied to the skin of a mammal such as a human patient, provides therapeutically effective blood plasma levels of felodipine to effectively treat hypertension in a human patient, wherein the transdermal device is maintained in contact with the patient's skin for at least 5 days, the transdermal delivery system maintaining an effective mean relative release rate to provide a therapeutic blood level of the felodipine within three days from the initiation of the dosing interval, and thereafter maintaining a therapeutic blood level until the end of at least the five-day dosing interval.

The invention is further directed to a transdermal felodipine device for the effective treatment of hypertension, which device, when applied to the skin of a patient maintained in contact with the patient's skin for at least 3 days, has an effective mean relative release rate to provide a therapeutic blood level of the felodipine within 36 hours from the initiation of the dosing interval, and thereafter maintains a therapeutic blood level until the end of at least the three-day dosing interval.

The invention is further directed in part to a transdermal felodipine device for the treatment of hypertension, which provides substantially zero order pharmacokinetics over a significant portion of the dosage interval.

The invention is further directed to a transdermal device and a method of effectively treating hypertension in a human patient, comprising applying the transdermal felodipine device to the skin of the patient and maintaining the transdermal delivery system in contact with the skin of a patient for at least 5 days, the transdermal delivery system maintaining an effective mean relative release rate to provide a substantially first order plasma level increase of felodipine from the initiation of the dosing interval until about 48 to about 72 hours after the initiation of the dosing interval; and thereafter providing an effective mean relative release rate to provide a substantially zero order plasma level fluctuation of felodipine until the end of at least the five-day dosing interval.

The invention is further directed to a transdermal felodipine device which when applied to the skin of a patient and maintained in contact with the patient's skin for at least 3 days, has an effective mean relative release rate to provide a substantially first order plasma level increase of felodipine from the initiation of the dosing interval until about 24 hours after the initiation of the dosing interval; and thereafter provides an effective mean relative release rate to provide a substantially zero order plasma level fluctuation of felodipine until the end of at least the three-day dosing interval.

The invention is further directed to a transdermal felodipine device and a method for lessening the incidence of side-effects in a patient associated with the oral administration of felodipine, wherein the method comprises administering the felodipine in a transdermal dosage form over at least twenty-four hours and thereby lessening the incidence of side effects.

The invention is further directed to a transdermal felodipine device and method which provides for reduced side-effects and avoids peak plasma concentrations of felodipine in a patient associated with the oral administration of felodipine (i.e., reduces the peak plasma level relative to immediate release orally delivered felodipine), via the administration of felodipine in a transdermal dosage form over at least twenty-four hours, thereby lessening the incidence of side effects and avoiding the peak plasma concentrations of felodipine.

It is yet a further object to provide a transdermal delivery system suitable for the above methods.

For example, the above methods can be achieved utilizing a transdermal therapeutic system for the administration of felodipine to the skin comprising a backing layer which is impermeable to the active substance, a pressure-sensitive adhesive reservoir layer, and optionally a removable protective layer, the reservoir layer by weight comprising 20 to 90% of a polymeric matrix, 0.1 to 30% of a softening agent, 0.1 to 20% of felodipine base or of a pharmaceutically acceptable salt thereof and 0.1 to 30% of a solvent for the felodipine or salt thereof.

Another alternative is to utilize a laminated composite for administering felodipine or a pharmaceutically acceptable salt thereof to an individual transdermally comprising (a) a polymer backing layer that is substantially impermeable to felodipine or the pharmaceutically acceptable salt thereof; and (b) a reservoir layer comprising an acrylate or silicon based pressure-sensitive adhesive, 0.1 to 20% of felodipine base or of a pharmaceutically acceptable salt thereof, 0.1 to 30% of an ester of a carboxylic acid acting as a softening agent and 0.1 to 30% of a solvent for felodipine having at least one acidic group.

The methods of the present invention are described in further detail in the following sections. Unless defined otherwise, all technical and scientific terms used herein have the same meaning as commonly understood by one of ordinary skill in the art to which this invention pertains. However, it should be understood that for purposes of the present invention, the following terms have the following meanings:

The term "effective treatment of hypertension" is defined for purposes of the present invention as a satisfactory reduction in or elimination of the symptoms associated with hypertension, along with the process of a tolerable level of side effects, as determined by the human patient.

Drug release from membrane-controlled systems may be defined as follows:

Amount released per area unit Q=const (zero order kinetics)

The term "mean relative release rate" is determined from the amount of drug released per unit time from the transdermal delivery system through the skin and into the bloodstream of a human patient. Mean relative release rate may be expressed, e.g., as $\mu g/cm^2/hr$. For purposes of the invention, it is understood that relative release rates may change between any particular time points within a particular dosing interval, and the term therefore only reflects the overall release rate during the particular dosing interval.

For purposes of the present invention, relative release rate should be considered synonymous with the term "flux rate".

The term "sustained release" is defined for purposes of the present invention as the release of the drug (felodipine) from the transdermal formulation at such a rate that blood (e.g., plasma) concentrations (levels) are maintained within the therapeutic range (above the minimum effective concentration) but below toxic levels over a period of time of about 3 days or longer.

The term "steady state" means that the blood plasma concentration curve for a given drug has been substantially repeated from dose to dose.

The term "minimum effective concentration" is defined for purposes of this invention as the minimum effective therapeutic blood plasma level of the drug at which at least some therapeutic effect in treating hypertension is achieved in a given patient.

The term "overage" means for the purposes of the present invention the amount of felodipine contained in a transdermal delivery system, which is not delivered to the patient. The overage is necessary for creating a concentration gradient by means of which the active agent (e.g., felodipine) migrates through the layers of the transdermal dosage form to the desired site on a patient's skin.

The term "first order" pharmacokinetics is defined as plasma concentrations, which increase over a specified time period.

The term "zero order" pharmacokinetics contemplates an amount of drug released from a felodipine formulation, which substantially maintains plasma concentrations at a relatively constant level. For purposes of the present invention, a relatively constant plasma concentration is defined as a concentration, which does not decrease more than about 30% over a 48 hour time period.

Drug release from membrane-controlled systems may be defined as follows:

Amount released per area unit Q=const (zero order kinetics)

The term "mean relative release rate" is determined from the amount of drug released per unit time from the transdermal delivery system through the skin and into the bloodstream of a human patient. Mean relative release rate may be expressed, e.g, as $\mu g/cm^2/hr$. For example, a transdermal delivery system that releases 10 mg of felodipine over a time period of 24 hours is considered to have a relative release rate of $4.1 \times 10^{-4}$ µg/hr. For purposes of the invention, it is understood that relative release rates may change between any particular time points within a particular dosing interval, and the term therefore only reflects the overall release rate during the particular dosing interval. For purposes of the present invention, relative release rate should be considered synonymous with the term "flux rate".

The term "sustained release" is defined for purposes of the present invention as the release of the drug from the transdermal formulation at such a rate that blood (e.g., plasma) concentrations (levels) are maintained within the therapeutic range (above the minimum effective drug concentration or "MEDC") but below toxic levels over a period of time of about 3 days or longer.

The term "steady state" means that the blood plasma concentration curve for a given drug has been substantially repeated from dose to dose.

The term "minimum effective concentration" is defined for purposes of this invention as the minimum effective therapeutic blood plasma level of the drug at which at least some therapeutic effect in treating hypertension is achieved in a given patient.

For purposes of the present invention, the term "felodipine" shall include felodipine base, pharmaceutically acceptable salts thereof, stereoisomers thereof, enantiomers thereof, ethers thereof, and mixtures thereof.

For purposes of this invention, the terms "transdermal delivery system" and "transdermal device" are interchangeable.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
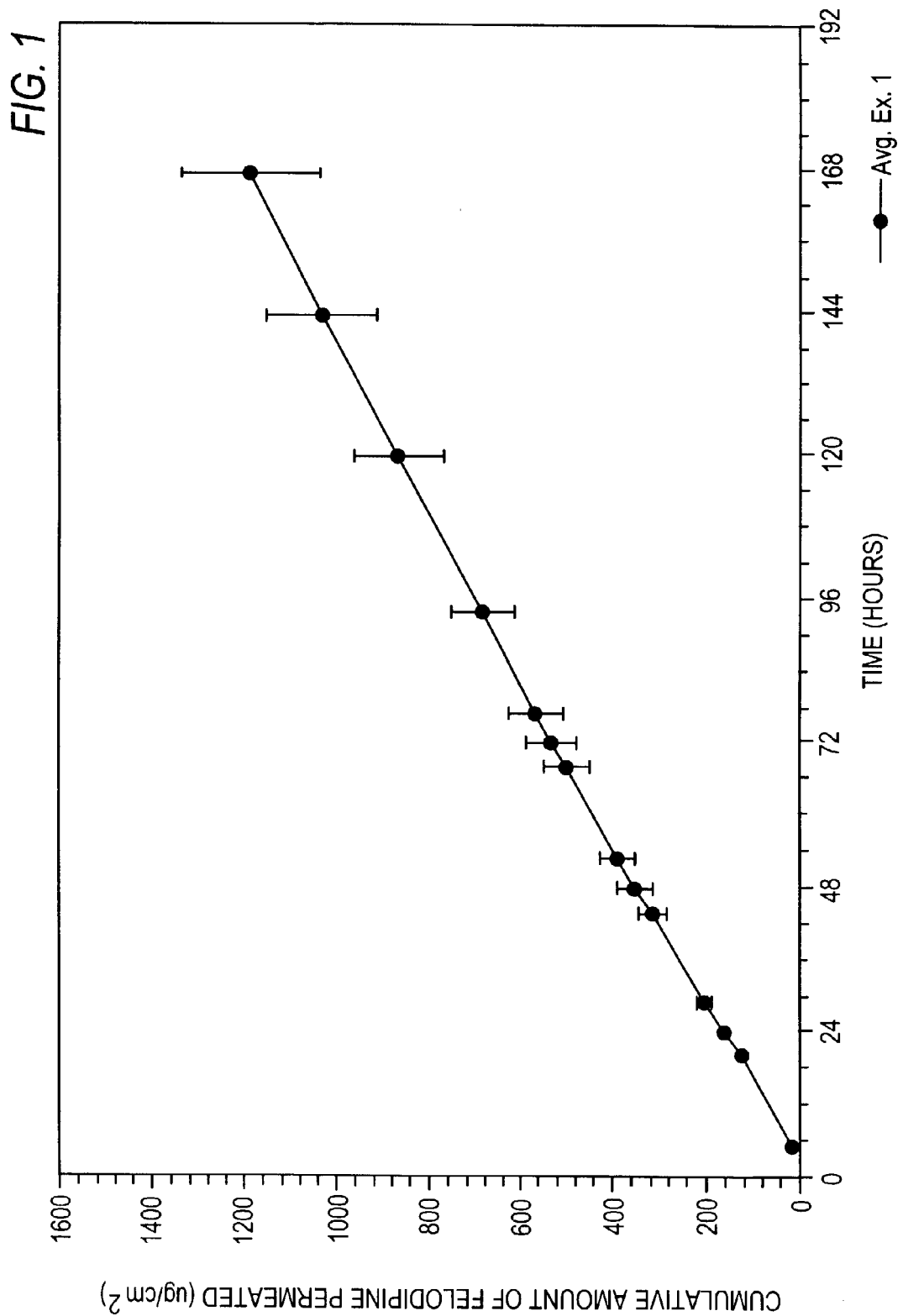
FIG. 1 is a graphical representation of the average cumulative amount of felodipine resulting from 4 permeation tests of Example 1 through human cadaver skin.
Figure 2:
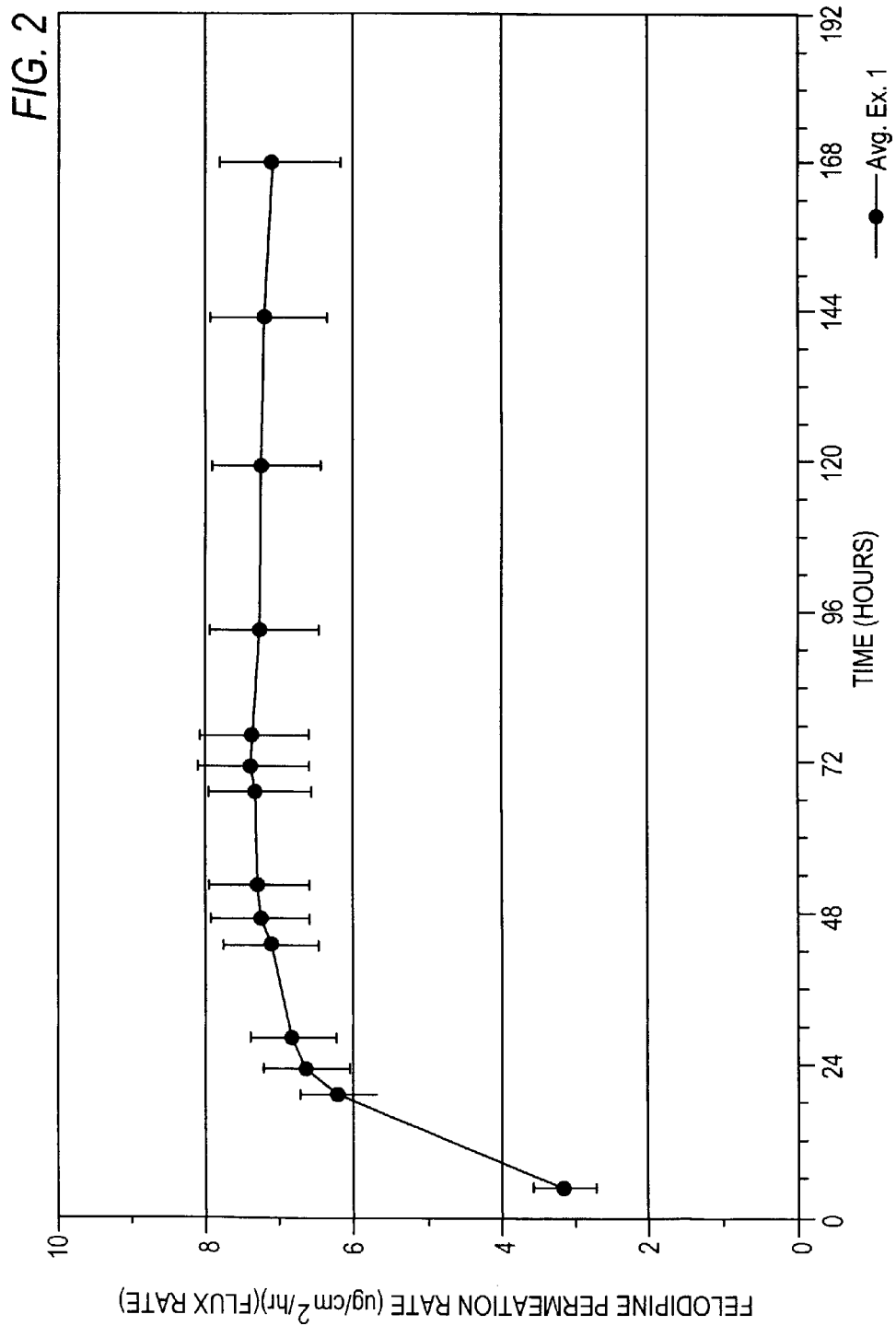
FIG. 2 is a graphical representation of the average felodipine permeation rate (flux rate) of Example 1 through human cadaver skin.
Figure 3:
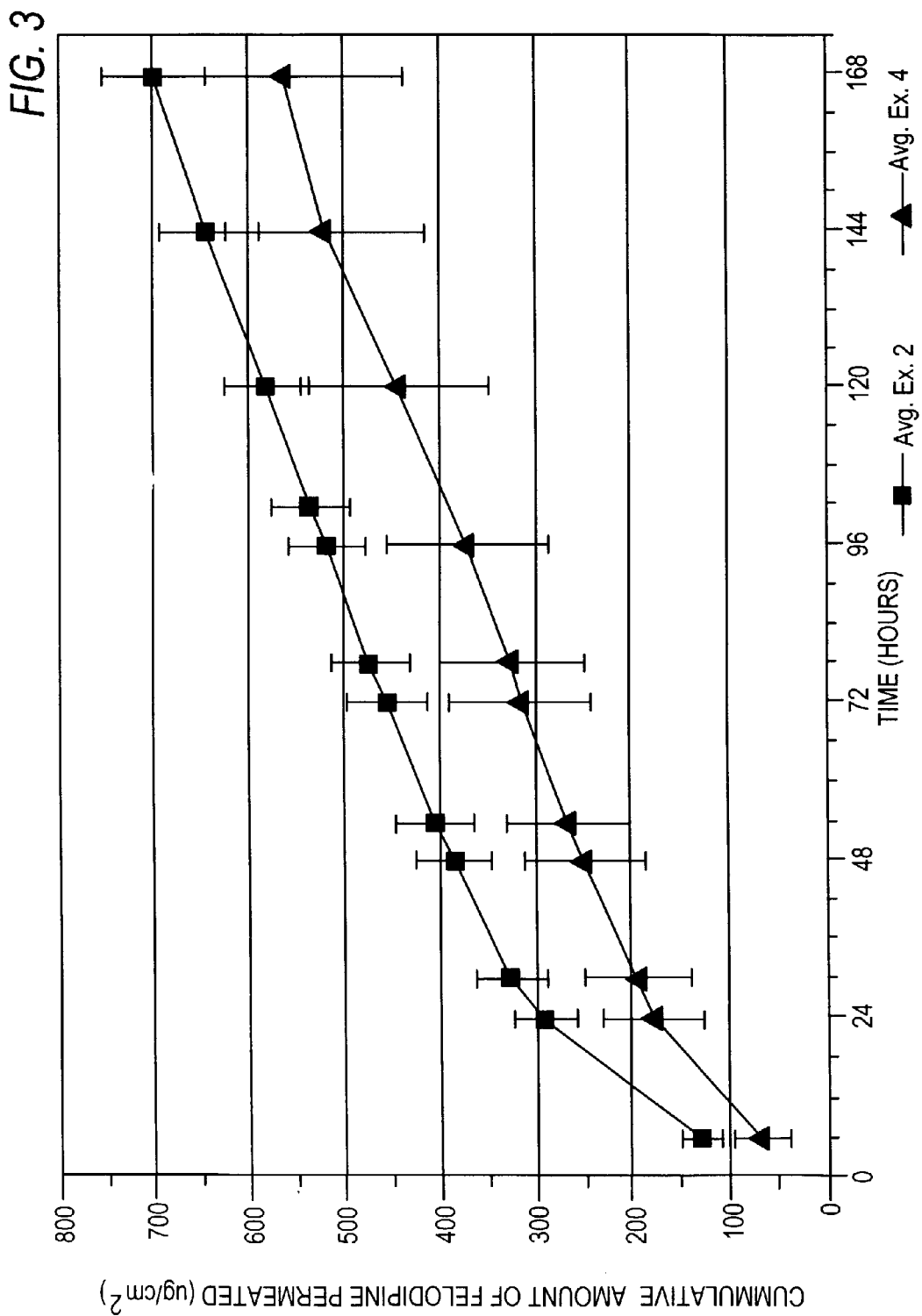
FIG. 3 is a graphical representation of the average cumulative amounts of felodipine resulting from permeation tests of Examples 2 and 4 trough human cadaver skin.
Figure 4:
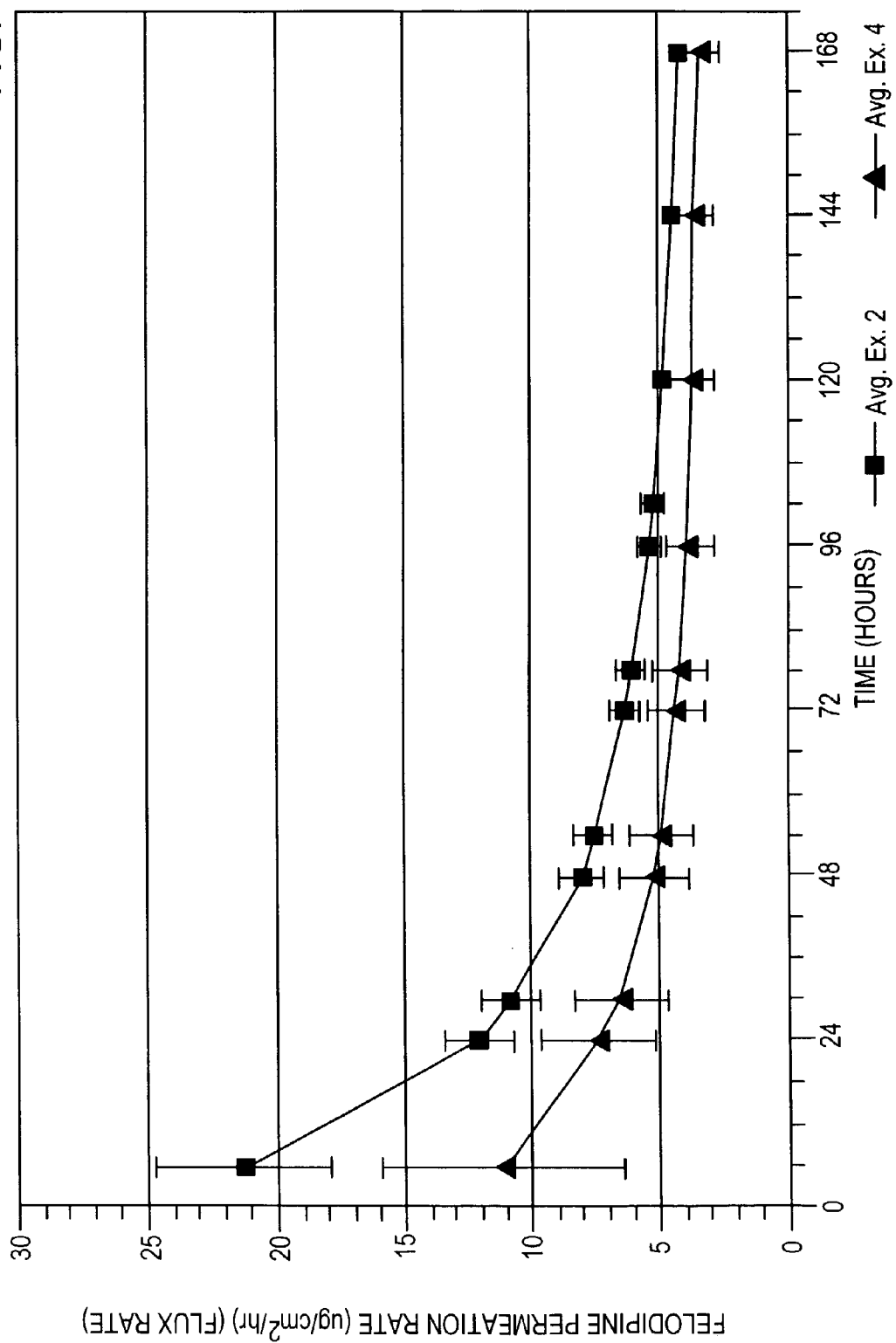
FIG. 4 is a graphical representation of the average felodipine permeation rates (flux rates) of Examples 2 and 4 trough human cadaver skin.
Figure 5:
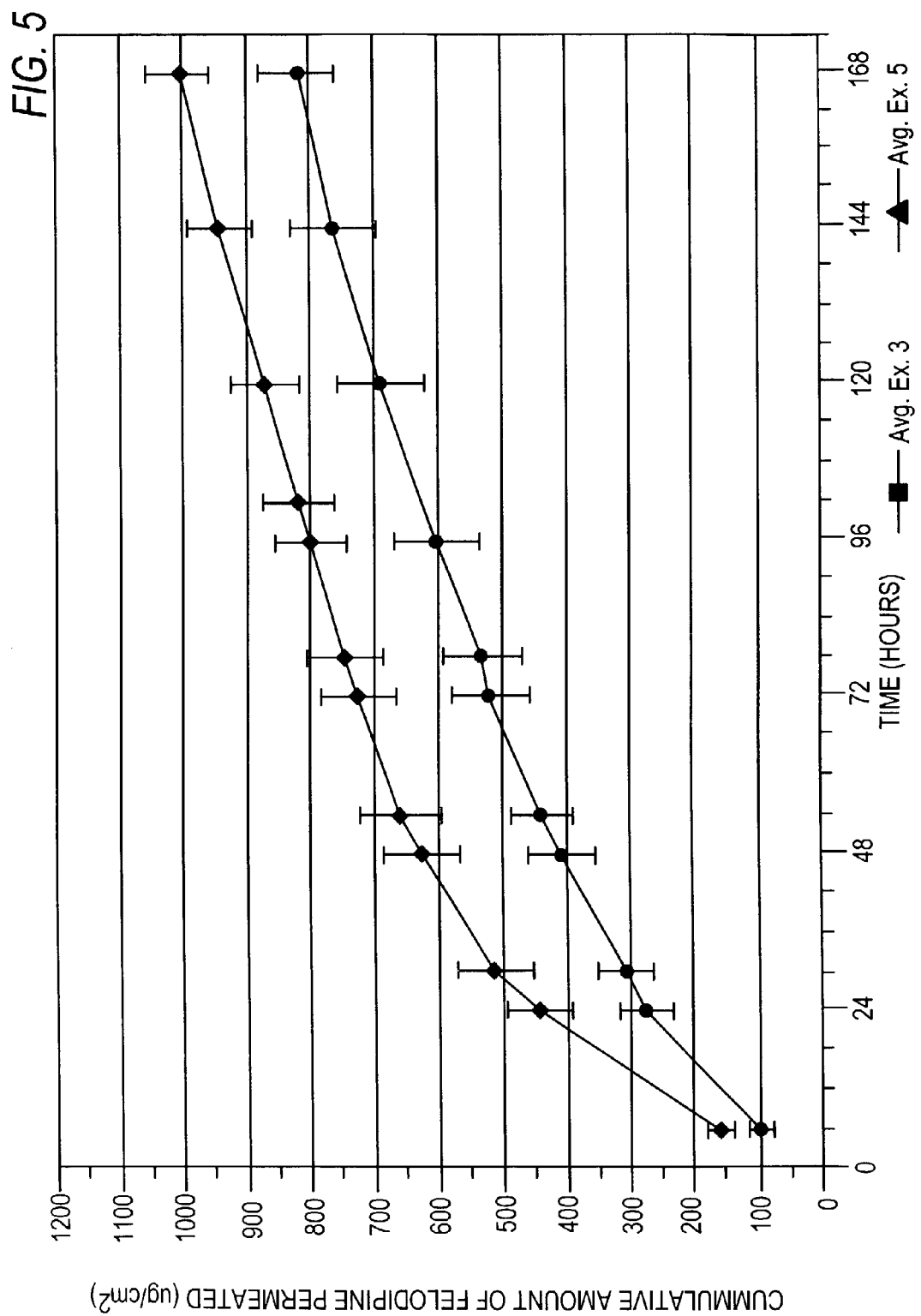
FIG. 5 is a graphical representation of the average cumulative amounts of felodipine resulting from permeation tests of Examples 3 and 5 trough human cadaver skin.
Figure 6:
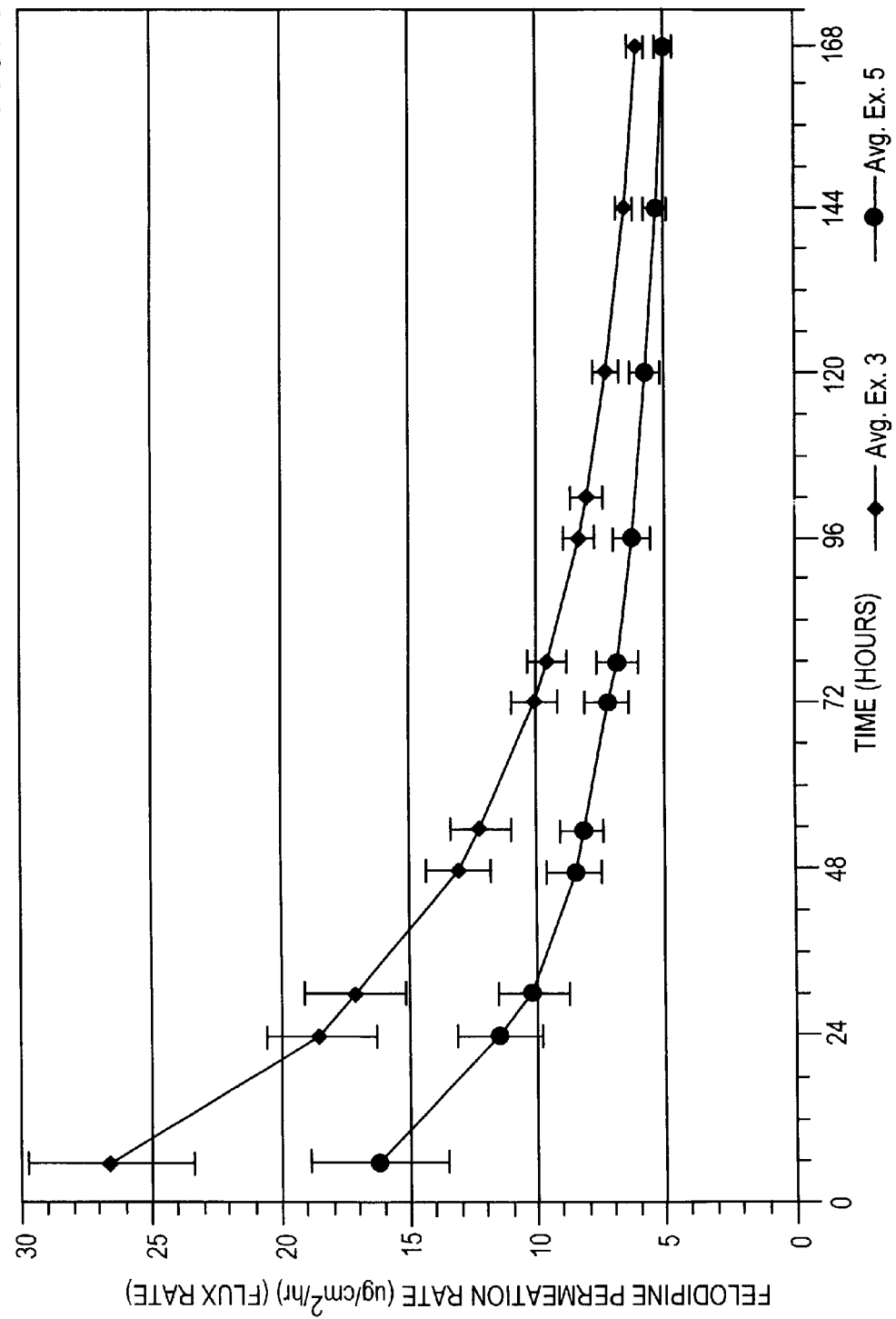
FIG. 6 is a graphical representation of the average felodipine permeation rates (flux rates) of Examples 3 and 5 trough human cadaver skin.
Figure 7:
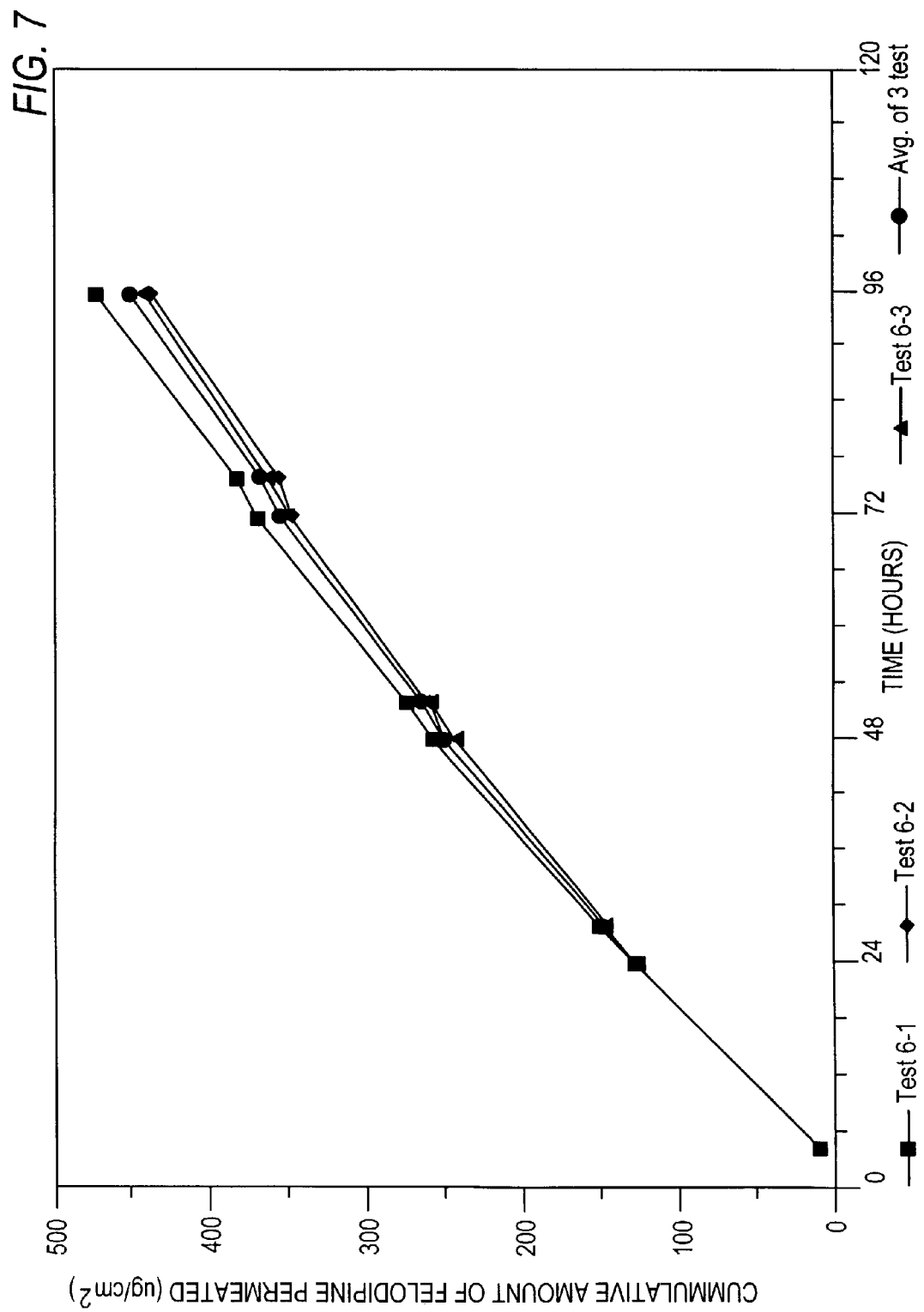
FIG. 7 is a graphical representation is a graphical representation of the cumulative amounts of felodipine resulting from 3 permeation tests of Example 6 through human cadaver skin.
Figure 8:
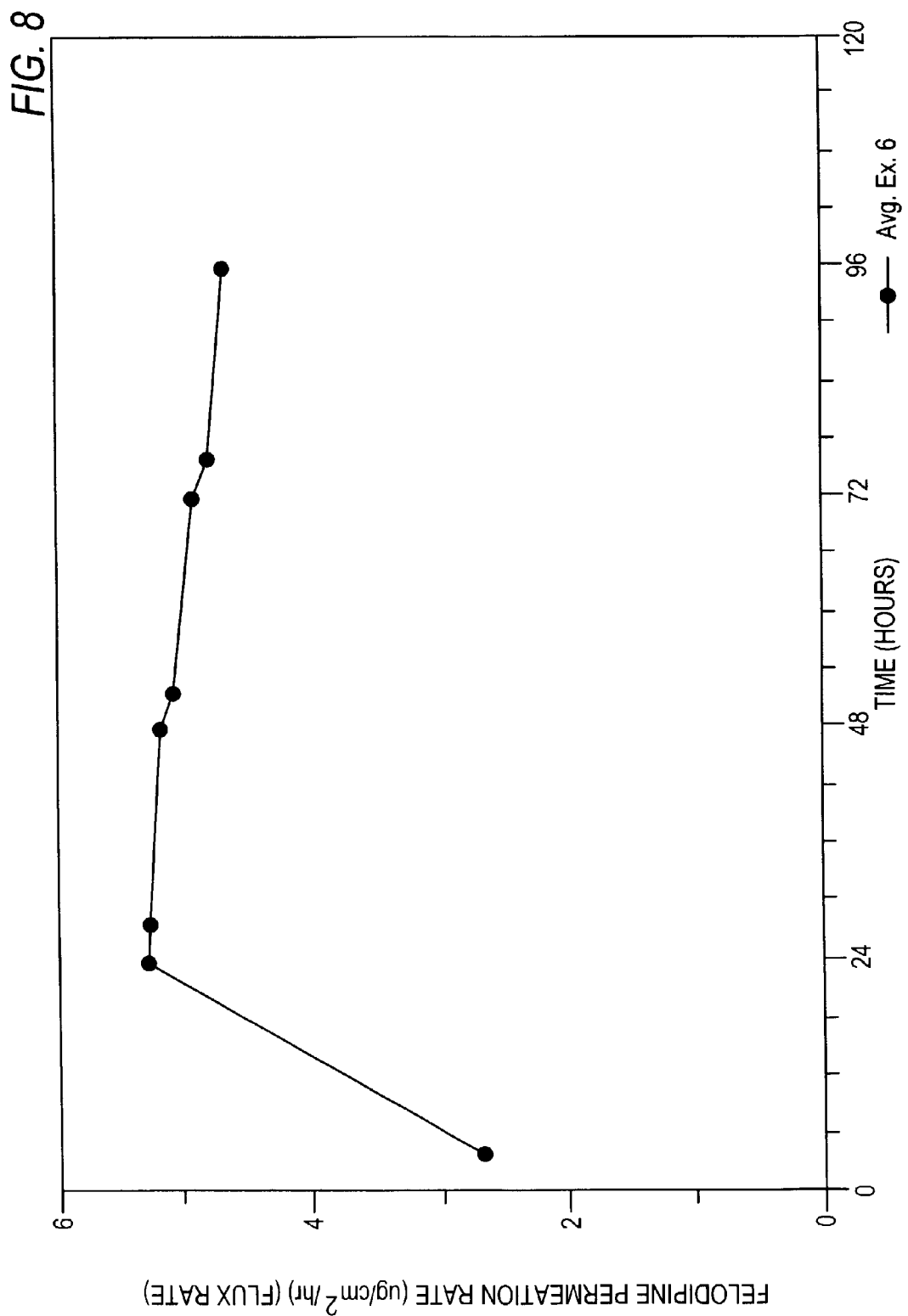
FIG. 8 is a graphical representation of the average felodipine permeation rate (flux rate) of Example 6 through human cadaver skin.
Figure 9:
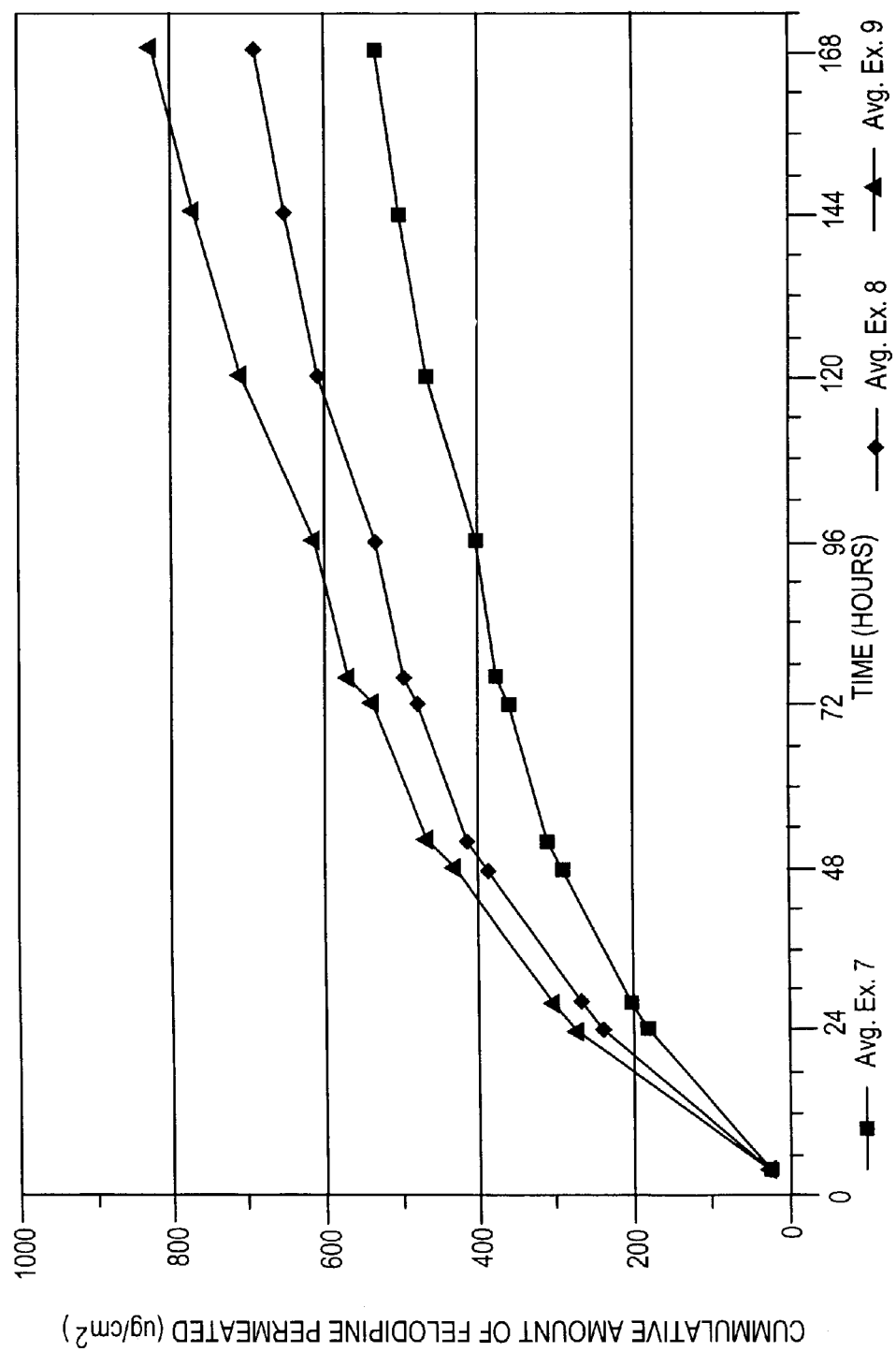
FIG. 9 is a graphical representation of the average cumulative amounts of felodipine resulting from permeation tests of Examples 7, 8 and 9 trough human cadaver skin.
Figure 10:
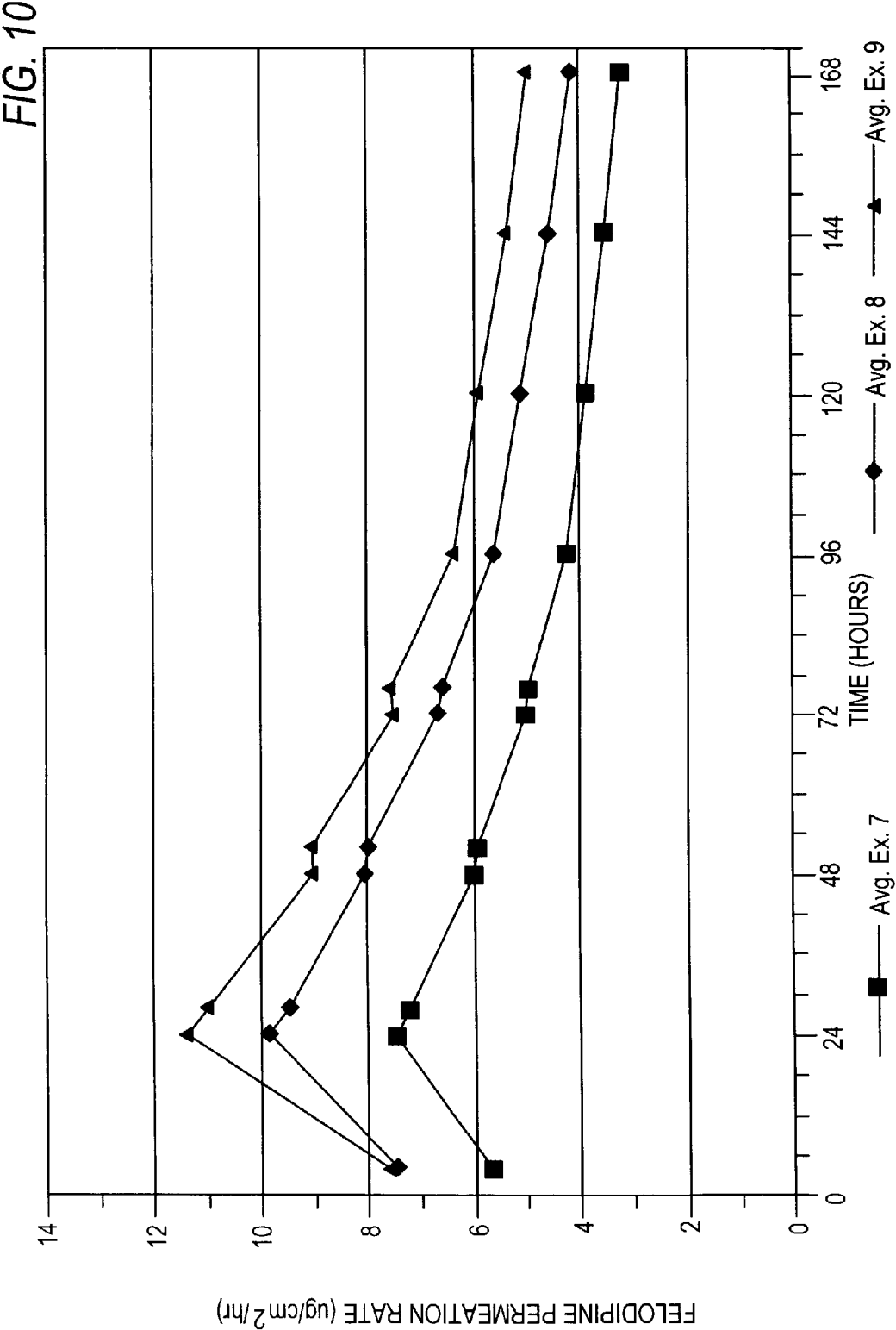
FIG. 10 is a graphical representation of the average felodipine permeation rates (flux rates) of Examples 7, 8 and 9 trough human cadaver skin.
Figure 11:
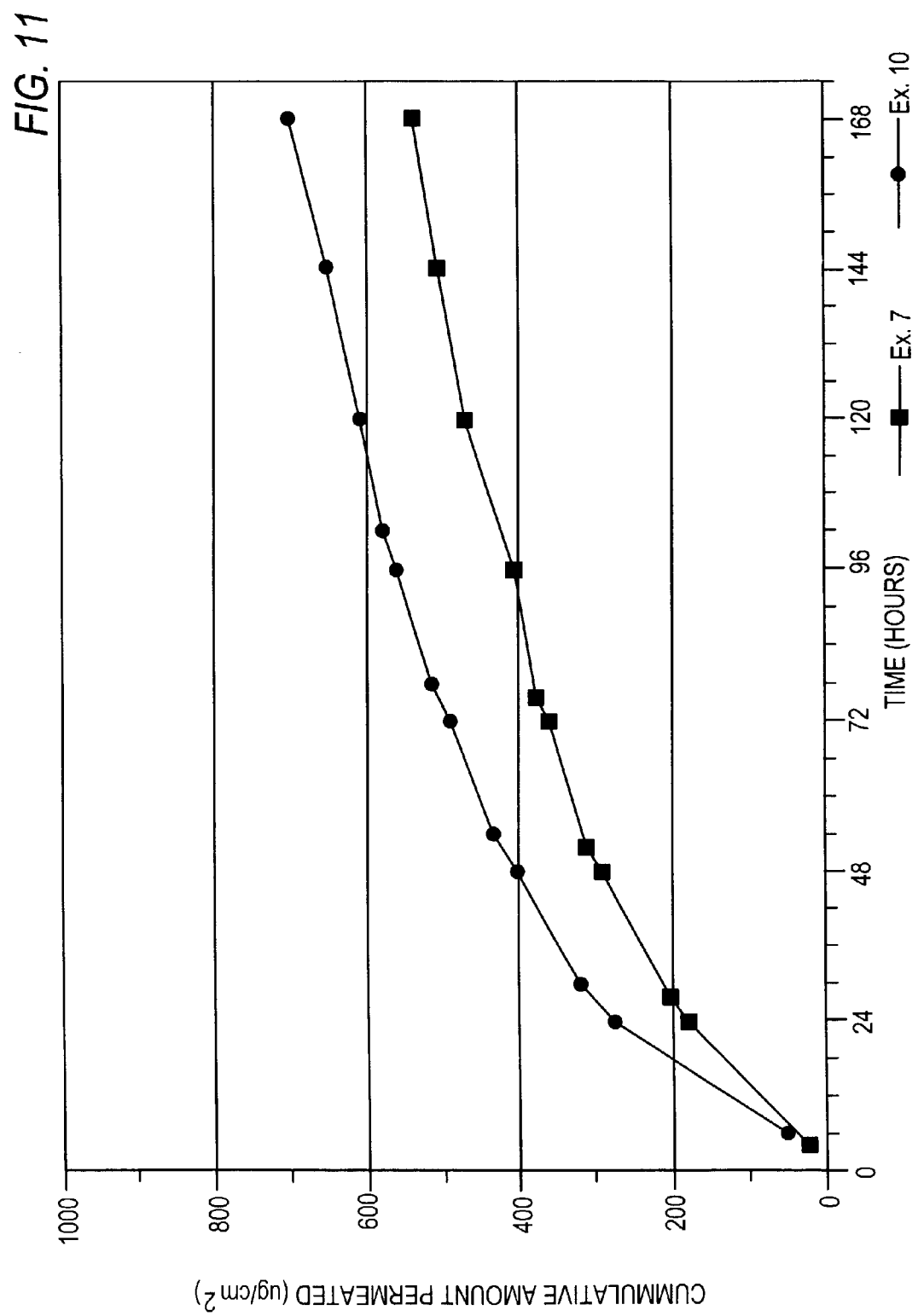
FIG. 11 is a graphical representation of the average cumulative amounts of felodipine resulting from the permeation tests of Examples 7 and 10 trough human cadaver skin.
Figure 12:
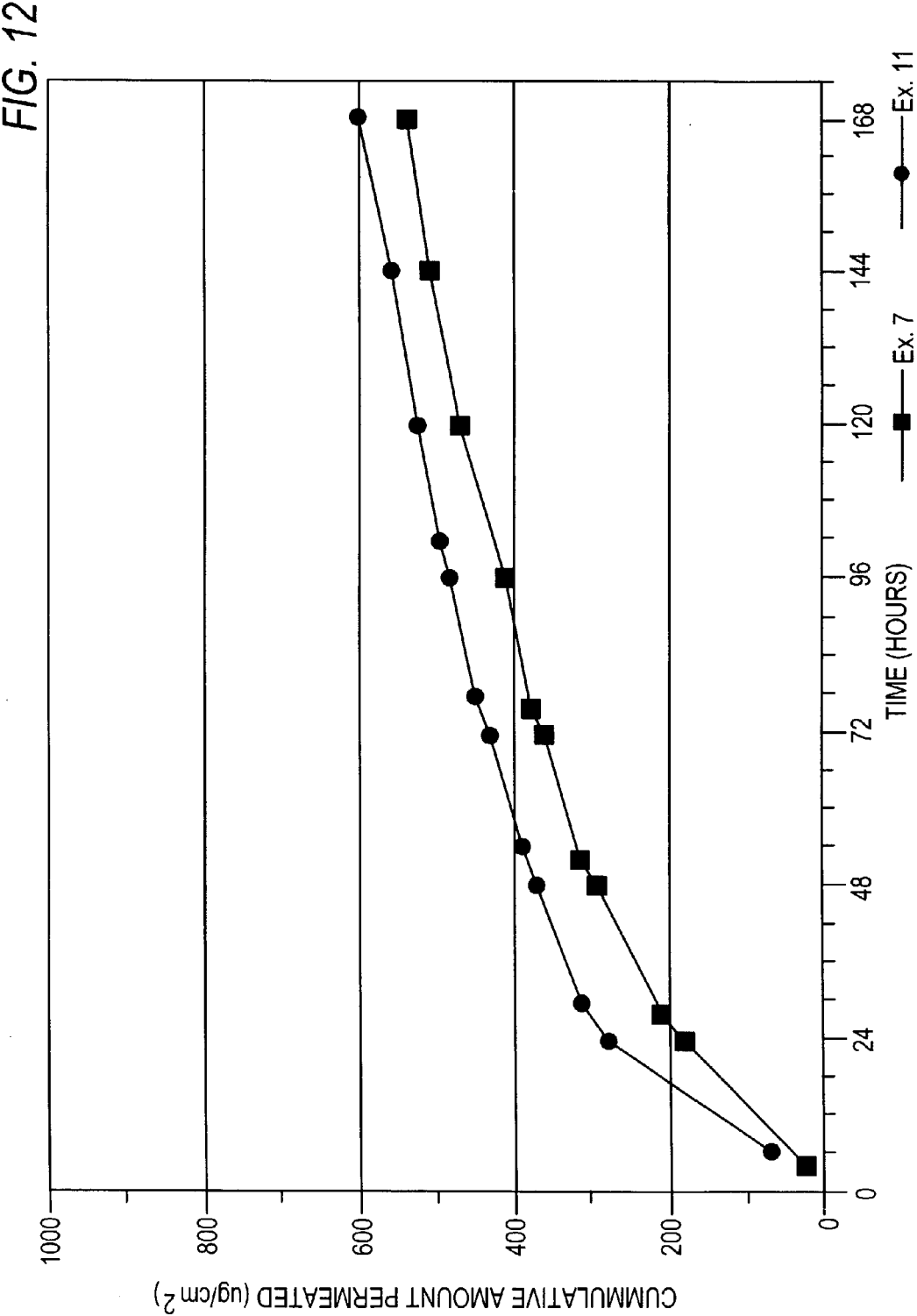
FIG. 12 is a graphical representation of the average cumulative amounts of felodipine resulting from the permeation tests of Examples 7 and 11 trough human cadaver skin.
Figure 13:
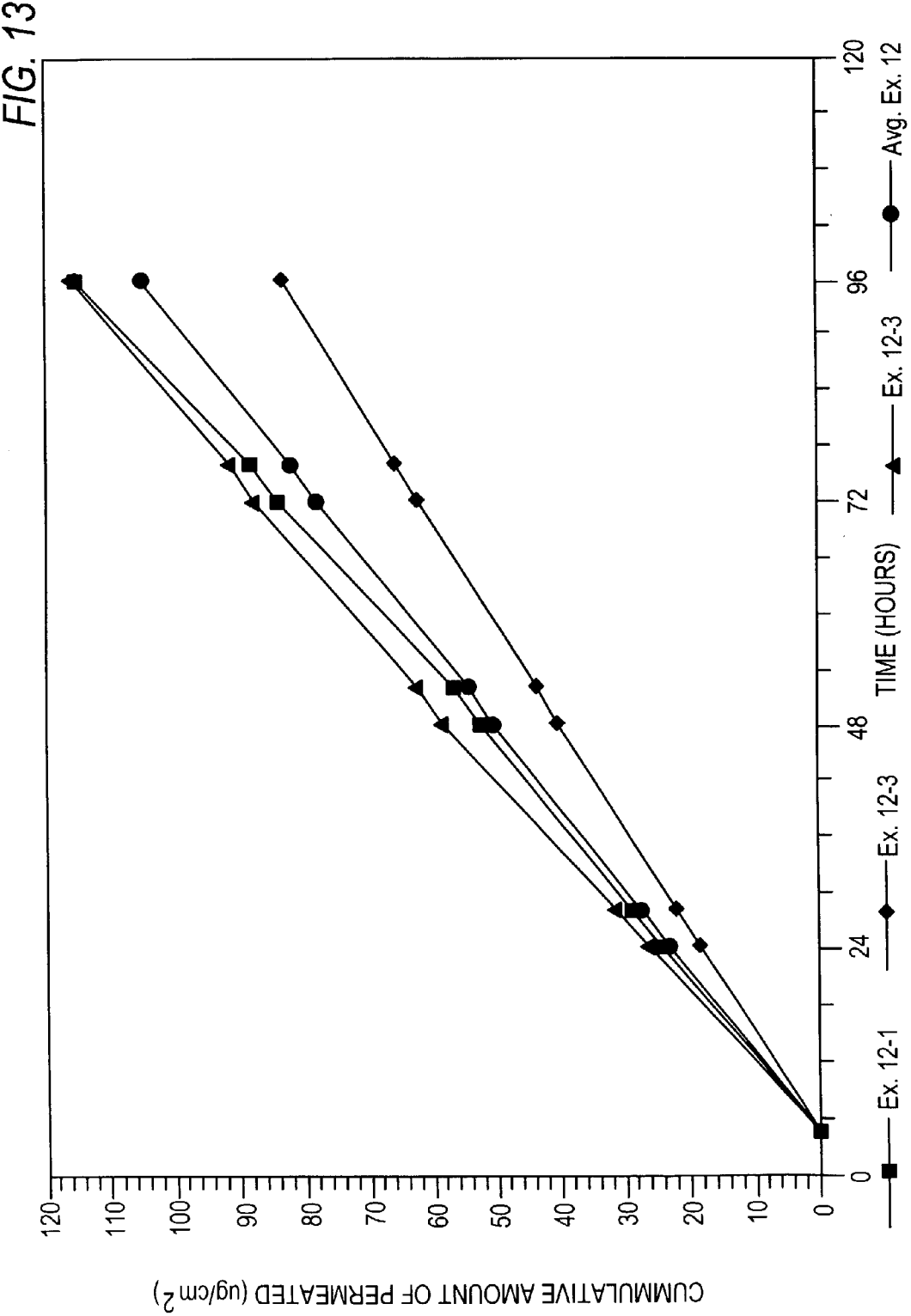
FIG. 13 is a graphical representation of the cumulative amounts of felodipine resulting from 3 permeation tests of Example 12 through human cadaver skin.
Figure 14:
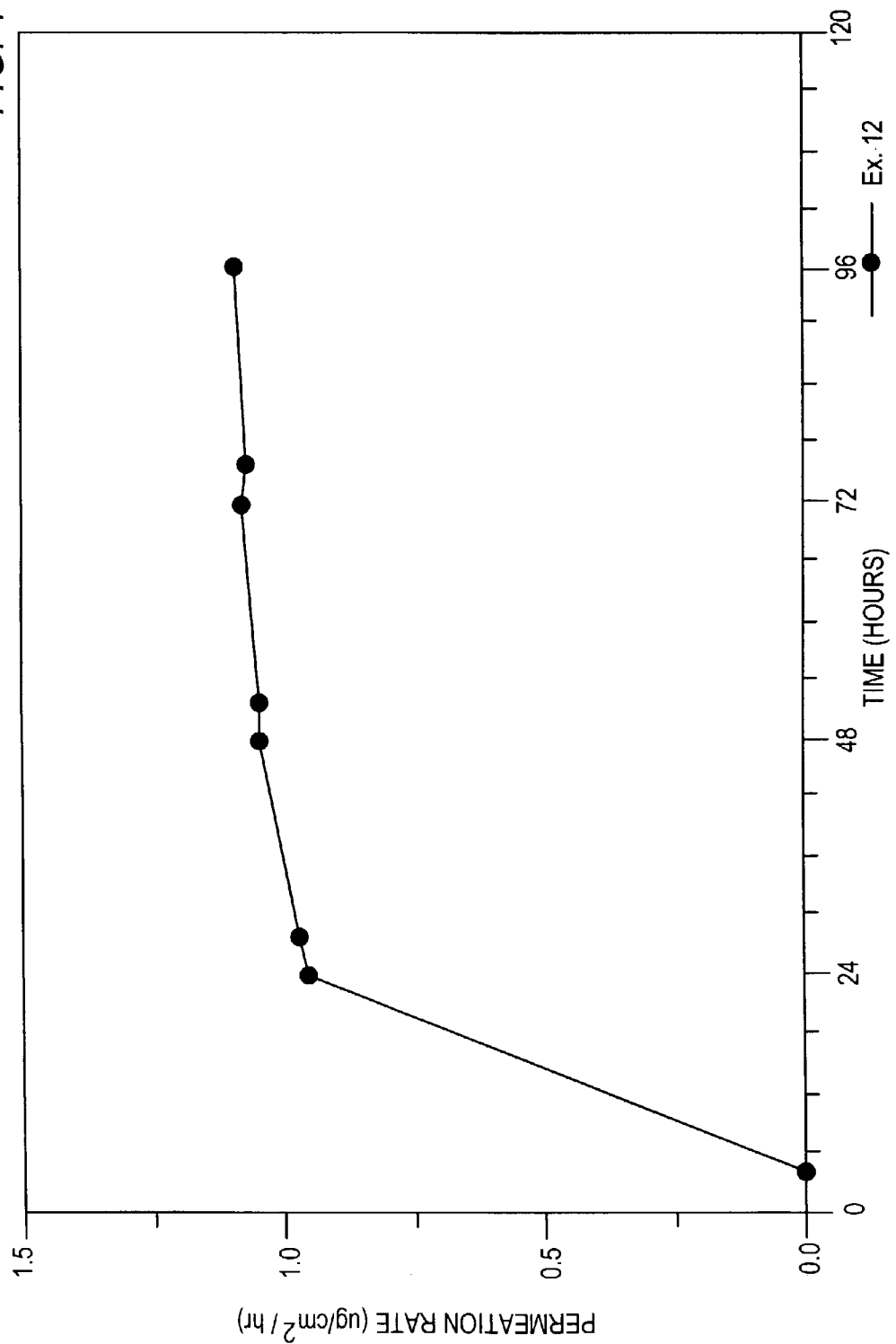
FIG. 14 is a graphical representation of the average permeation rate (flux rate) of felodipine resulting from 3permeation tests of Example 12 through human cadaver skin.
Figure 15:
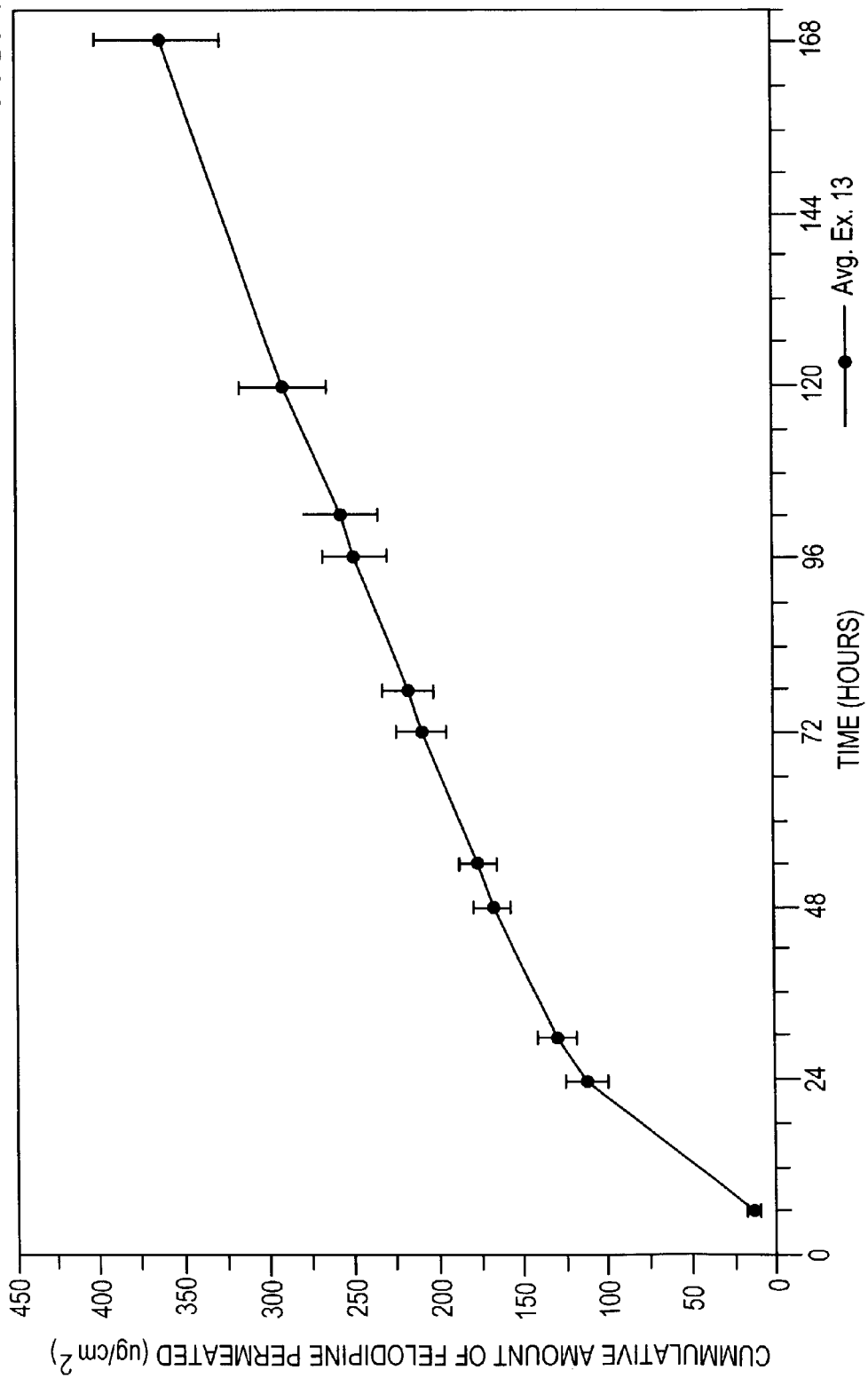
FIG. 15 is a graphical representation of the average cumulative amount of felodipine resulting from 3 permeation tests of Example 13 through human cadaver skin.
Figure 16:
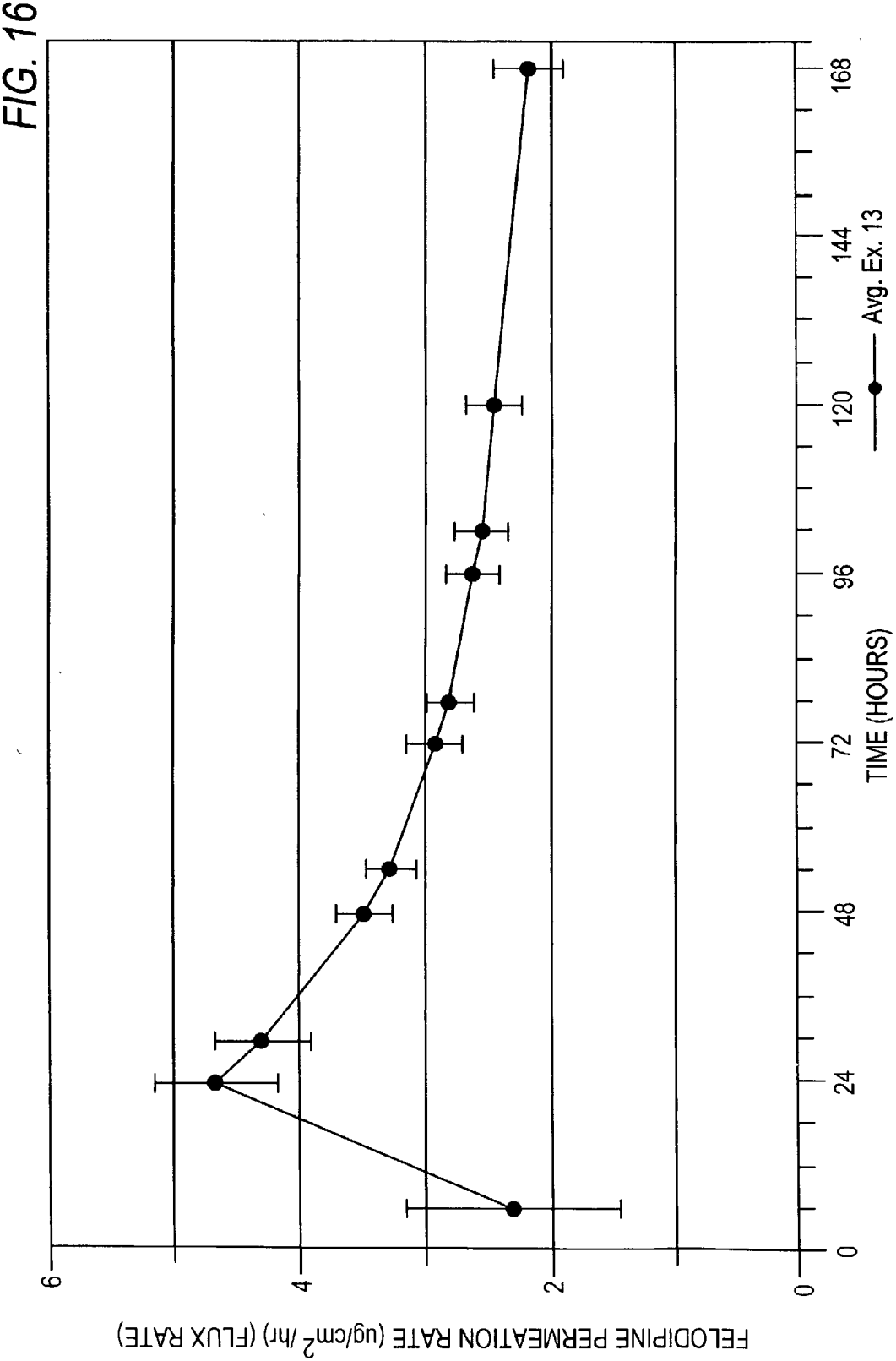
FIG. 16 is a graphical representation of the average felodipine permeation rate (flux rate) of Example 13 through human cadaver skin.

Transdermal delivery of active agents is measured in terms of "relative release rate" or "flux", i.e., the rate of penetration of the active agent through the skin of an individual. Skin flux may be generally determined from the following equation:

$$dm/dT = J = P*C$$

where J is the skin flux, P is the permeability coefficient and C is the concentration gradient across the membrane, assumed to be the same as the donor concentration. m represents the amount of drug entering the blood stream. The variable dm/dT represent the change in amount of drug entering the blood stream and change over time.

It is well understood in the art of transdermal delivery systems that in order to maintain a desired flux rate for a desired dosing period, it is necessary to include an overage of active agent in the transdermal delivery system in an amount that is substantially greater than the amount to be delivered to the patient over the desired time period. For example, to maintain the desired flux rate for a three day time period, it is considered necessary to include much greater than 100% of a three-day dose of an active agent in a transdermal delivery system. This overage is necessary for creating a concentration gradient by means of which the active agent migrates through the layers of the transdermal delivery system to the desired site on a patient's skin. The remainder of the active agent remains in the transdermal delivery system. It is only the portion of active agent that exits the transdermal delivery system that becomes available for absorption into the skin. The total amount of active agent absorbed into the patient's blood stream is less than the total amount available. The amount of overage to be included in a transdermal delivery system is dependent on these and other factors known to the skilled artisan.

It has been found that it is possible to treat hypertension according to the present invention by providing a transdermal delivery system containing a sufficient amount of felodipine to provide a desired relative release rate for at least about 3 days, and after single administration (application) of the transdermal dosage form, leaving the dosage form on the skin for approximately a 3 to 8 day time period, thereby resulting in the flux being maintained over the prolonged period and effective blood plasma levels and management of hypertension being maintained over the prolonged period. Preferably, the desired flux is maintained at least about 5, preferably at least about 7 days after application of the transdermal delivery system.

Transdermal dosage forms used in accordance with the invention preferably include a backing layer made of pharmaceutically acceptable material, which is impermeable to felodipine. The backing layer preferably serves as a protective cover for the active agent, e.g. felodipine and may also provide a support function. Examples of materials suitable for making the backing layer are films of high and low density polyethylene, polypropylene, polyvinylchloride, polyurethane, polyesters such as poly(ethylene terephthalate), metal foils, metal foil laminates of such suitable polymer films, textile fabrics, if the components of the reservoir cannot penetrate the fabric due to their physical properties and the like. Preferably, the materials used for the backing layer are laminates of such polymer films with a metal foil such as aluminum foil. The backing layer can be any appropriate thickness, which will provide the desired protective and support functions. A suitable thickness will be from about 10 to about 200 microns. Desirable materials and thickness will be apparent to the skilled artisan.

Matrix Systems

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylene vinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof.

Preferred materials for inclusion in the polymer matrix layer are silicone elastomers of the general polydimethylsiloxane structures, (e.g., silicone polymers). Preferred silicone polymers cross-link and are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable cross-linking agent. Suitable crosslinking agents include, e.g., tetrapropoxy silane.

Preferred transdermal delivery systems used in accordance with the methods of the present invention include an adhesive layer to affix the dosage form to the skin of the patient for a desired period of administration, e.g., about 3 to about 8 days. If the adhesive layer of the dosage form fails to provide adhesion for the desired period of time, it is possible to maintain contact between the dosage form with the skin by, for instance, affixing the dosage form to the skin of the patient with an adhesive tape, e.g, surgical tape. It is not critical for purposes of the present invention whether adhesion of the dosage form to the skin of the patient is achieved solely by the adhesive layer of the dosage form or in connection with a peripheral adhesive source, such as surgical tape, provided that the dosage form is adhered to the patient's skin for the requisite administration period.

The adhesive layer preferably includes using any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers. In other preferred embodiments of the invention, the adhesive is a pressure-sensitive contact adhesive, which is preferably hypoallergenic.

The transdermal dosage forms, which can be used in accordance with the present invention, may optionally include a permeation-enhancing agent. Permeation enhancing agents are compounds, which promote penetration and/or absorption of the felodipine into the blood stream of the patient. A non-limiting list of permeation enhancing agents includes polyethylene glycols, surfactants, and the like.

Alternatively, permeation of felodipine may be enhanced by occlusion of the dosage form after application to the desired site on the patient with, e.g. an occlusive bandage. Permeation may also be enhanced by removing hair from the application site by, e.g. clipping, shaving or use of a depilatory agent. Another permeation enhancer is heat. It is thought that heat enhancement can be induced by, among other things, using a radiating heat form, such as an infrared lamp, onto the application site after application of the transdermal dosage form. Other means of enhancing permeation of felodipine such as the use of iontophoretic means are also contemplated to be within the scope of the present invention.

A preferred transdermal dosage form which may be used in accordance with the present invention includes a non-permeable backing layer made, for example, of polyester; an adhesive layer made, for example of a polyacrylate; and a matrix containing the felodipine and other desirable pharmaceutical aids such as softeners, permeability enhancers, viscosity agents and the like.

The active agent may be included in the device in a drug reservoir, drug matrix or drug/adhesive layer. Preferably, the active agent is felodipine or a pharmaceutically acceptable salt thereof.

Certain preferred transdermal delivery systems also include a softening agent. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, cocprylic acids glycerol and 1,2-propanediol, which can also be etherified by polyethylene glycols.

A felodipine solvent may also be included in the transdermal delivery systems of the present invention. Preferably, the solvents dissolve the felodipine to a sufficient extent thereby avoiding complete salt formation. A non-limiting list of suitable solvents include those with at least one acidic group. Particularly suitable are monoesters of dicarboxylic acids such as monomethylglutarate and monomethyladipate.

Other pharmaceutically acceptable compounds which may be included in the reservoir or matrix include: solvents, for example alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective layer. The removable protective layer is removed prior to application, and consists of the materials used for the production of the backing layer described above provided that they are rendered removable, for example, by a silicone treatment. Other removable protective layers, for example, are polytetra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The composition of the transdermal dosage forms used in accordance with the invention and the type of device used are not considered critical to the method of the invention, provided that the device delivers the active agent, e.g. felodipine, for the desired time period and at the desired flux rate and/or the desired delivery rate of the transdermal dosage form.

Certain transdermal dosage forms for use in accordance with the present invention are described in U.S. Pat. No. 5,240,711 (Hille, et. al.; assigned to LTS Lohmann Therapie-Systeme GmbH & Co.), hereby incorporated by reference. Such transdermal delivery systems may be a laminated composite having an impermeable backing layer containing felodipine, e.g., instead of buprenorphine, and optionally a permeation enhancer combined with a pressure-sensitive adhesive. A preferred transdermal dosage form in accordance with the '711 patent includes: (i) a polyester backing layer which is impermeable to the drug; (ii) a polyacrylate adhesive layer; (iii) a separating polyester layer; and (iv) a matrix containing felodipine, a solvent for the felodipine, a softener and a polyacrylate adhesive. The felodipine solvent may or may not be present in the final formulation. The transdermal delivery device described therein includes a backing layer, which is impermeable to the active substance, a pressure-sensitive adhesive reservoir layer, and optionally, a removable protective layer. Preferably, the reservoir layer includes about 10 to about 95%-wt polymeric material, about 0.1 to about 40%-wt softener, about 0.1 to about 30%-wt felodipine. A solvent for the felodipine base or pharmaceutically acceptable salt thereof may be included as about 0.1 to about 30%-wt.

The transdermal delivery system may also be prepared in accordance with the disclosure of International Patent Application No. WO 96/19975 (Hille, et. al.; assigned to LTS Lohmann Therapie-Systeme GMBH), hereby incorporated by reference, where felodipine is substituted for buprenorphine as an active agent. In this device, the felodipine transdermal delivery device contains resorption-promoting auxiliary substances. The resorption-promoting auxiliary substance forms an under cooled mass. The delivery system contains 10% felodipine base, 10–15% acid (such as levulinic acid), about 10% softener (such as oleyoleate); 55–70% polyacrylate; and 0–10% polyvinylpyrollidone (PVP).

Reservoir Devices

Alternatively, the transdermal device may be a reservoir system. A reservoir system transdermal drug delivery patch comprises several different components. An exemplary construction includes a backing layer, an active drug and optional permeation enhancing solvent gel, a membrane, a skin contact adhesive layer, and a protective release coated liner film. Characteristics of each component are set forth below:

Backing Film: This layer is exposed to the external environment when the system is worn on the skin surface. It is impervious to penetration of the active drug contained within the system preventing the escape of the active drug through the backing film. The backing film serves as barrier layer. Moisture, soaps, lotions and other elements are prevented from entering the system and diluting the active ingredients or altering the release characteristics of the system. The active drug and solvent are contained within the system to perform its designated function. The backing film also forms one half of the chamber, which contains the active drug reservoir. The backing film must be capable of being suitably attached to the membrane in order to form the reservoir chamber. Typical attachment methods include thermal, ultrasonic polymer heat seal or welding, and adhesive bonding. Necessary mechanical properties include a low compliance for conformability to the skin surface and elasticity to allow for movement with the skin surface. Typical thickness is in the range of 0.5–25.0 mil. Wide ranges of homogenous, woven, and non-woven polymer or composite materials are suitable as backing films.

Membrane: The membrane in combination with the backing film forms the chamber, which contains the active drug reservoir. The membrane is attached to the backing film, and provides a support surface for the skin contact adhesive. The membrane can be a homogenous polymer film, or a material with a porous structure. The membrane may also be designed to control the transport rate of the active drug and/or the permeation enhancing solvent. Necessary mechanical properties include a low compliance for conformability to the skin surface and elasticity to allow for movement with the skin surface. Typical thickness is in the range of 0.25–30.0 mil (1 mil=0.001 inch), and more preferably in the range of 0.5 to 25.0 mil. Wide ranges of homogenous, porous, woven, and non-woven polymer or composite materials are suitable as membranes and known in the art.

Active Drug Reservoir: The active drug is combined with a liquid vehicle to fill the reservoir chamber. A range of solvents can be used for the liquid vehicle. The solvents can be chosen to optimize skin permeation of the active (enhancers) or to optimize the permeation characteristics of the membrane or the adhesion of the skin contact adhesive. A viscosity-increasing agent is often included in the vehicle to aide in the handling and system manufacturing process. The composition of the vehicle must be compatible with the other components of the system. The vehicle may be in the form of a solution, suspension, cream, lotion, gel, physical mixture or emulsion. This list is not meant to be exhaustive.

Skin Contact Adhesive: The system is affixed to the skin with a skin contact adhesive. The adhesive may cover the entire surface of the system membrane, be applied in an intermittent pattern, or only to the perimeter of the system. The adhesive composition must be of materials suitable for skin contact without creating intolerable adverse effects such as excessive skin irritation or sensitization. Adequate adhesion to the membrane and skin are also necessary. The adhesive must also possess enough cohesive integrity to remain completely on the membrane upon removal of the system. The adhesive is applied in a thickness to provide a weight of 0.025 to 50.0 mg/cm$^2$, more preferably 0.25 to 5.0 mg/cm$^2$ and most preferably 0.3 to 0.6 mg/cm$^2$. Typical materials include silicone, polyisobutylene (PIB), and acrylates dissolved in organic solvents, aqueous emulsions, or directly applied by hot melt processing.

Release Coated Liner Film: The liner film is removed from the system before application to the skin surface. The liner film serves the function as a protective barrier to the skin contact adhesive prior to use. The coating on the liner provides a release capability for the adhesive, allowing separation of the liner from the adhesive. A coating is not necessary if the liner material is readily removed from the adhesive without disrupting the reservoir system. Typical thickness is in the range of 0.5–25.0 mil. A wide range of homogenous, woven, and non-woven paper, polymer or composite materials are suitable as liner films. Release coatings are typically composed of paraffin, polyethylene, silicone or fluorocarbons.

In other embodiments, the transdermal delivery system may be a plaster such as that described in U.S. Pat. No. 5,225,199 to Hidaka et al., hereby incorporated by reference. Such plasters include a film layer including a polyester film of about 0.5 to about 4.9 μm thickness, about 8 to about 85 g/mm strength, respectively in the two directions intersecting substantially at right angles, about 30 to about 150% elongation, in the two directions intersecting substantially at right angles and an elongation ratio of A to B of about 1.0 to about 5.0, wherein A and B represent data in two directions intersecting at right angles, and A is greater than B and wherein said polyester film includes about 0.01 to about 1.0% by weight, based on the total weight of the polyester film, of solid fine particles in which the average particle size is about 0.001 to about 3.0 μm and an adhesive layer which is composed of an adhesive containing transdermally absorbable drugs; wherein the adhesive layer is laminated on said film layer over the surface in about 2 to about 60 μm thickness. The average particle size is substantially not more than 1.5 times the thickness of the polyester film.

The transdermal delivery system used in the present invention may also be prepared in accordance with U.S. Pat. No. 5,879,701, issued Mar. 9, 1999 to Audett, et al., hereby incorporated by reference, wherein solubilization enhancer compositions are provided which facilitate transdermal administration of basic drugs from transdermal systems composed of nonpolar adhesive materials. The solubilization enhancing composition is particularly useful in facilitating the administration of basic drugs using transdermal systems worn for at least four days containing drug reservoirs comprised of nonpolar materials such as polyisobutylene adhesives or the like. The solubilizing enhancing composition itself is preferably a liquid, which is an isomeric acid mixture. Examples of suitable solubilizers include, but are not limited to, oleic acid dimer and neodecanoic acid, with oleic acid dimer particularly preferred. The solubilizer constitutes at least about 0.10 wt. % of the reservoir, and preferably represents on the order of 0.25 wt. % to 1.0 wt. % of the reservoir. The amount of enhancer composition present in the drug formulation will depend on a number of factors, e.g., the strength of the particular enhancer composition, the desired increase in skin permeability, and the amount of drug, which is necessary to deliver.

The pharmacokinetic information for felodipine is available in the literature. The adult oral dosage for felodipine is 10 mg/day. The bioavailability for the drug is approximately 20%, expressed as fraction, 0.20 of the oral dose made available to the blood stream from gastrointestinal absorption. A release rate for a felodipine transdermal delivery system was calculated from this data. 0.20 of the oral 10 mg daily dose provides 2.0 mg of felodipine available into the blood stream. Therefore, an equal dose is required to be delivered transdermally. 2.0 mg/day is converted to 2000 mcg/24 hours. This would require delivery of 83.3 mcg/hour. The largest desirable surface area for a transdermal patch is about 40 $cm^2$. Dividing 83.3 mcg/hour/40 $cm^2$ by 40, yields a release rate of 2.1 mcg/hour/$cm^2$ of transdermal patch surface area. To account for drug elimination, further pharmacokinetic data and physiological data were required. The plasma concentration at steady state for felodipine is 0.002 mcg/ml. The physiological clearance rate is 48,000 ml/hour. The dosing rate is obtained from the product of the steady state concentration of felodipine and a representative clearance rate. This product is 96 mcg/hour. The largest desirable surface area for a transdermal patch is about 40 $cm^2$. Dividing 96 mcg/hour/40 $cm^2$ by 40, yields a release rate of 2.4 mcg/hour/$cm^2$ of transdermal patch surface area. One of skill would expect a larger input rate or flux to maintain a steady state concentration in consideration of the loss of drug in the plasma due to elimination. A confirmatory calculation for flux requires further pharmacokinetic parameters. The volume of distribution for felodipine is 700,000 ml and the half-life is 14 hours. The elimination rate constant is 0.693/half-life. The product of steady state concentration, volume of distribution and steady state concentration yields a rate of 69.3 mcg/hour. The largest desirable surface area for a transdermal patch is about 40 $cm^2$. Dividing 69.3 mcg/hour/40 $cm^2$ by 40, yields a release rate of 1.73 mcg/hour/$cm^2$ of transdermal patch surface area.

Any type of transdermal delivery system may be used in accordance with the methods of the present invention so long as the desired pharmacokinetic and pharmacodynamic response(s) are attained over at least 3 days, e.g., from about 5 to about 8 days. Preferable transdermal delivery systems include e.g., transdermal patches, transdermal plasters, transdermal discs, iontophoretic transdermal devices and the like.

DETAILED DESCRIPTION OF THE PREFERRED EMBODIMENTS

The following examples illustrate various aspects of the present invention. They are not to be construed to limit the claims in any manner whatsoever.

Overview of Method of Manufacture: Matrix System

The following general method is used in the following examples in which the transdermal device tested is a matrix system (device):

Step 1: Preparation of the active drug vehicle/solvent/adhesive matrix. Active drug is combined with the liquid vehicle components and the adhesive components using appropriate mixing techniques well known in the art. Simple mechanical mixers, motionless mixers, homogenizers, high shear mixers, and magnetic mixing devices can be employed.

Step 2: Preparation of the active drug/adhesive matrix coated liner. Active drug/adhesive matrix coating is done with continuous web based equipment on a commercial scale. Small sheet batches can be made readily in the lab manually. A mechanism for applying a controlled thickness coating of the active drug/adhesive matrix onto the liner is employed. If solvent-based adhesives are used, a procedure for driving off the solvent and drying the active drug/adhesive matrix is employed. The open surface of the active drug/adhesive matrix on the liner must be protected during processing. A second intermediate liner can be used to cover this active drug/adhesive matrix surface.

Step 3: Laminating of the membrane to active drug/adhesive and/or liner. The membrane is typically applied on line after solvent removal on a commercial scale. This avoids the need for a second liner. A separate web and a heat and/or pressure lamination station bonds the two layers. The membrane provides a non-stick surface to the open side of the adhesive and allows for further processing in a roll form.

Overview of the Manufacture of Reservoir Devices

The following general method is used in the following examples in which the transdermal device tested is a reservoir system (device):

Step 1: Preparation of the adhesive coated liner. Adhesive coating is done with continuous web based equipment on a commercial scale. Small sheet batches can be made readily in the lab manually. A mechanism for applying a controlled thickness coating of the adhesive onto the liner is employed. If solvent-based adhesives are used, a procedure for driving off the solvent and drying the adhesive is employed. The open surface of the adhesive on the liner must be protected during processing. A second intermediate liner can be used to cover this adhesive surface.

Step 2: Laminating of the membrane to adhesive and/or liner. The membrane is typically applied on line after solvent removal on a commercial scale. This avoids the need for a second liner. A separate web and a heat and/or pressure lamination station bonds the two layers. The membrane provides a non-stick surface to the open side of the adhesive and allows for further processing in a roll form.

Step 3: Preparation of the active vehicle/solvent combination. Active drug is combined with the liquid vehicle components using appropriate mixing techniques well known in the art. Simple mechanical mixers, motionless mixers, homogenizers, high shear mixers, and magnetic mixing devices can be employed. Other ingredients are also incorporated at this time. These may include permeation enhancers and viscosity thickeners, for example.

Step 4: Finalizing the delivery system utilizing the form, fill and seal process incorporating the reservoir and backing film. This process can be carried out in either a horizontal or vertical plane. The horizontal mode requires a thickened viscosity of the reservoir vehicle, while the vertical mode can handle liquid vehicles of minimal viscosity. In the horizontal mode a dispensing head places a fixed volume drop of the drug vehicle onto the surface of the membrane. The backing film is then placed over the drop of vehicle, and then bound to the membrane to enclose the active/vehicle. A heated die is commonly used to form a heat seal welded bond. In web based systems a die cutting and packaging station often follows.

in-vitro Skin Permeation Test Method

The test methods utilized in the following examples involve the use of a permeation cell. Several permeation cell designs are available for in-vitro permeation testing. These include "Franz cells", "Valia-Chien cells", and "Bronaugh cells". Each cell design shares several common characteristics. All cells are made with a definable surface area for permeation. All cells contain two chambers and a clamping mechanism to hold the test membrane positioned between the two cell chambers. Several exemplary test membranes include mouse skin and human cadaver skin. The membrane may be oriented in either the horizontal or vertical plane based on the cell special arrangement. One chamber serves as a reservoir (donor) for the drug to be tested; the second is a place where the permeated drug is accumulated (receptor). The receptor is often chosen to mimic the physiological conditions found beneath the membrane in-vivo. In the case where a complete transdermal system is the donor, it is clamped between the two chambers and only the receptor chamber is filled.

Calculation of the permeation rate (J) requires knowledge of the concentration (C) of the drug in the receptor chamber, the permeation area (A), sampling interval (t) and the receptor volume (V). The equation below is typical:

$$J = CV/At \text{ where}: J = \text{micrograms}/\text{cm}^2\text{-hr}$$
$$C = \text{micrograms}/\text{ml}$$
$$V = \text{ml}$$
$$A = \text{cm}^2$$
$$t = \text{hr}$$

Only the drug concentration and testing time vary in typical experiments. The drug concentration is determined by any appropriate analytical technique such as high performance liquid chromatograpy, gas chromatograpy, column elusion, or ultraviolet spectrophotometry. Other considerations in the testing system may include temperature control systems, receptor stirring systems, flow through receptor chambers, and automated sampling equipment utilizing pumps and fraction collectors. Partial receptor sampling protocols have been used in situations where the sensitivity of the analytical method for determining the drug concentration was less than optimal.

Sample testing protocols for felodipine follow.

| | |
|---|---|
| Cells | Valia Chien |
| Membrane | Human cadaver skin |
| A (cm2) | 0.636 |
| V (ml) | 4.0 |
| receptor | Ethanol/water 40/60 |
| sampling points | 6, 24, 48, 72, 120, 144, 168 hours |
| sampling mode: | partial, 0.6 ml per point, replace with fresh receptor. |

HPLC conditions for determination of drug concentration.

| | |
|---|---|
| Column | Hypersil C18, 5 μm, 4.6 mm × 25 cm |
| Mobile phase | Acetonitrile/Buffer 70/30 |
| Buffer: | 0.01M phosphate @ pH 4.5 |
| Flow rate | 1 ml/min |
| UV detection | 237 nm |
| Injection volume | 20 microl |
| Retention time | 5.0 min |

EXAMPLE 1

A Felodipine reservoir and adhesive formulation was prepared having the formulation set forth in Table 1A below:

TABLE 1A

| Ingredient | Amount (gm) |
|---|---|
| Felodipine | 1.0 |
| Ethanol | 22.0 |
| Water | 27.0 |
| Total | 50.0 |
| Polyethylene membrane | |
| Silicone adhesive | |

The formulation of Example 1 was prepared and incorporated into a permeation testing apparatus according to the following procedure:

1. Felodipine is dissolved with ethanol and water and the solution is placed into the donor cell.
2. The polyethylene membrane is coated with a silicone adhesive and placed against the donor cell. The adhesive coated membrane is positioned opposite from the donor cell.
3. Thereafter, the human cadaver skin is placed between the adhesive coated polyethylene membrane and the receptor cell and the apparatus is secured.

The formulation of Example 1 was tested using a permeation cell with definable surface area for permeation. The receptor of the permeation cell was Ethanol:water (40:60) and the test substrate through which transdermal delivery was sought was human cadaver skin. Samples of 1.0 ml were taken at time intervals set out in Table 1B. These samples were tested for felodipine concentration using high performance liquid chromatography (HPLC). The HPLC conditions for determination of drug concentration are set forth below:

HPLC conditions for determination of felodipine concentration.

| | |
|---|---|
| Column | Hypersil C18, 5 μm, 4.6 mm × 25 cm |
| Mobile phase | Acetonitrile/Buffer 70/30 |
| Buffer: | 0.01M phosphate @ pH 4.5 |
| Flow rate | 1 ml/min |
| UV detection | 237 nm |
| Injection volume | 20 microl |
| Retention time | 5.0 min |

Four replicate tests were conducted as in Example 1 (1-1, 1-2, 1-3, 1-4) giving the results listed in Table 1B below:

TABLE 1B

| | | | μg/cm² | | |
|---|---|---|---|---|---|
| Hours | Test 1-1 | Test 1-2 | Test 1-3 | Test 1-4 | Average of all 4 tests | Std Dev |
| 5 | 16.611 | 12.946 | 18.032 | 15.448 | 15.759 | 2.153 |
| 20 | 135.630 | 117.674 | 128.331 | 112.386 | 123.505 | 10.455 |
| 24 | 175.266 | 152.028 | 163.546 | 144.055 | 158.724 | 13.625 |
| 29 | 217.579 | 188.997 | 203.093 | 179.139 | 197.202 | 16.768 |
| 44 | 350.066 | 293.706 | 316.102 | 286.074 | 311.487 | 28.703 |
| 48 | 391.569 | 325.124 | 349.833 | 319.258 | 346.446 | 32.870 |
| 53 | 435.926 | 359.183 | 386.294 | 354.876 | 384.070 | 37.263 |
| 68 | 561.320 | 456.850 | 493.185 | 462.905 | 493.585 | 47.885 |
| 72 | 600.145 | 485.137 | 524.621 | 495.586 | 526.372 | 51.941 |
| 77 | 642.980 | 515.838 | 559.107 | 531.361 | 562.322 | 58.673 |
| 94 | 777.340 | 614.863 | 668.878 | 647.212 | 677.073 | 70.433 |
| 120 | 990.946 | 769.437 | 837.548 | 836.397 | 858.582 | 93.811 |
| 144 | 1190.839 | 908.827 | 985.583 | 995.354 | 1020.151 | 120.190 |
| 168 | 1385.558 | 1042.131 | 1124.715 | 1145.671 | 1174.519 | 147.622 |

Based on the permeation results of Example 1, listed in Table 1B, the following flux results listed in Table 1C below were obtained:

TABLE 1C

| | | | μg/cm²/hr | | |
|---|---|---|---|---|---|
| Hours | Test 1-1 | Test 1-2 | Test 1-3 | Test 1-4 | Average of all 4 tests | Std Dev |
| 5 | 3.322 | 2.589 | 3.606 | 3.090 | 3.152 | 0.431 |
| 20 | 6.782 | 5.884 | 6.417 | 5.619 | 6.175 | 0.523 |
| 24 | 7.303 | 6.335 | 6.814 | 6.002 | 6.613 | 0.568 |
| 29 | 7.503 | 6.517 | 7.003 | 6.177 | 6.800 | 0.578 |
| 44 | 7.956 | 6.675 | 7.184 | 6.502 | 7.079 | 0.652 |
| 48 | 8.158 | 6.773 | 7.288 | 6.651 | 7.218 | 0.685 |
| 53 | 8.225 | 6.777 | 7.289 | 6.696 | 7.247 | 0.703 |
| 68 | 8.255 | 6.718 | 7.253 | 6.807 | 7.258 | 0.704 |
| 72 | 8.335 | 6.738 | 7.286 | 6.883 | 7.311 | 0.721 |
| 77 | 8.350 | 6.699 | 7.261 | 6.901 | 7.303 | 0.736 |
| 94 | 8.270 | 6.541 | 7.116 | 6.885 | 7.203 | 0.749 |
| 120 | 8.258 | 6.412 | 6.980 | 6.970 | 7.155 | 0.782 |
| 144 | 8.270 | 6.311 | 6.844 | 6.912 | 7.084 | 0.835 |
| 168 | 8.247 | 6.203 | 6.695 | 6.819 | 6.991 | 0.879 |
| $F_{5-168}$ | 8.438 | 6.303 | 6.825 | 7.044 | 7.152 | 0.912 |
| CORR | 1.000 | 0.998 | 0.998 | 1.000 | 0.999 | |

EXAMPLE 2

A Felodipine reservoir and adhesive formulation was prepared having the formulation set forth in Table 2A below:

TABLE 2A

| Ingredient | Amount (gm) |
|---|---|
| Felodipine | 0.35 |
| Ethanol | 22.0 (95%) |
| Water | 27.0 |
| Total | 49.35 |
| Polyethylene membrane | |
| Silicone adhesive | |

The formulation of Example 2 was prepared and incorporated into a permeation testing apparatus according to the same procedure as in Example 1.

The formulation of Example 2 was tested as in Example 1. Sample size and HPLC conditions were the same as in Example 1. Three replicate tests were conducted as in Example 1 (2-1, 2-2, 2-3) giving the results listed in Table 2B below:

TABLE 2B

| | | | μg/cm² | | |
|---|---|---|---|---|---|
| Hours | Test 2-1 | Test 2-2 | Test 2-3 | Average of all 3 tests | Std Dev |
| 6 | 146.891 | 107.042 | 128.790 | 127.574 | 19.952 |
| 24 | 318.265 | 254.631 | 298.089 | 290.328 | 32.519 |
| 30 | 356.152 | 285.942 | 334.140 | 325.411 | 35.910 |
| 48 | 419.283 | 340.057 | 390.594 | 383.311 | 40.112 |
| 54 | 441.157 | 359.774 | 410.041 | 403.657 | 41.065 |
| 72 | 490.563 | 410.714 | 457.479 | 452.919 | 40.119 |
| 78 | 509.280 | 429.123 | 475.152 | 471.185 | 40.225 |
| 96 | 555.008 | 474.763 | 519.868 | 516.546 | 40.225 |
| 102 | 572.311 | 491.097 | 538.296 | 533.901 | 40.785 |
| 120 | 618.214 | 533.222 | 582.911 | 578.116 | 42.698 |
| 144 | 686.036 | 591.927 | 641.327 | 639.763 | 47.074 |
| 168 | 749.047 | 645.200 | 693.499 | 695.915 | 51.956 |

Based on the permeation results of Example 2, listed in Table 2B, the following flux results listed in Table 2C below were obtained:

TABLE 2C

| | | | μg/cm²/hr | | |
|---|---|---|---|---|---|
| Hours | Test 2-1 | Test 2-2 | Test 2-3 | Average of all 3 tests | STD DEV |
| 6 | 24.482 | 17.840 | 21.465 | 21.262 | 3.325 |
| 24 | 13.261 | 10.610 | 12.420 | 12.097 | 1.355 |
| 30 | 11.872 | 9.531 | 11.138 | 10.847 | 1.197 |
| 48 | 8.735 | 7.085 | 8.137 | 7.986 | 0.836 |
| 54 | 8.170 | 6.662 | 7.593 | 7.475 | 0.760 |
| 72 | 6.813 | 5.704 | 6.354 | 6.291 | 0.557 |
| 78 | 6.529 | 5.502 | 6.092 | 6.041 | 0.516 |
| 96 | 5.781 | 4.945 | 5.415 | 5.381 | 0.419 |
| 102 | 5.611 | 4.815 | 5.277 | 5.234 | 0.400 |
| 120 | 5.152 | 4.444 | 4.858 | 4.818 | 0.356 |
| 144 | 4.764 | 4.111 | 4.454 | 4.443 | 0.327 |
| 168 | 4.459 | 3.840 | 4.128 | 4.142 | 0.309 |
| $F_{6-168}$ | 3.273 | 2.993 | 3.072 | 3.113 | 0.144 |
| CORR | 0.973 | 0.978 | 0.970 | 0.974 | |
| $F_{48-168}$ | 2.721 | 2.536 | 2.533 | 2.597 | 0.107 |

EXAMPLE 3 (38)

A Felodipine reservoir and adhesive formulation was prepared having the formulation set forth in Table 3A below:

TABLE 3A

| Ingredient | Amount (gm) |
| --- | --- |
| Felodipine | 0.35 |
| Ethanol | 22.0 (95%) |
| Water | 27.0 |
| Total | 49.35 |
| Polyethylene membrane | |
| Silicone adhesive | |

The formulation of Example 3 was prepared and incorporated into a permeation testing apparatus according to the same procedure as in Example 1.

The formulation of Example 3 was tested as in Example 1. Sample size and HPLC conditions were the same as in Example 1. Three replicate tests were conducted as in Example 1 (3-1, 3-2, 3-3) giving the results listed in Table 3B below:

TABLE 3B

| | μg/cm² | | | | |
| --- | --- | --- | --- | --- | --- |
| Hours | Test 3-1 | Test 3-2 | Test 3-3 | Average of all 3 tests | Std Dev |
| 6 | 169.393 | 137.617 | 171.512 | 159.507 | 18.987 |
| 24 | 479.007 | 366.231 | 465.646 | 443.628 | 50.154 |
| 30 | 554.838 | 447.557 | 537.259 | 513.218 | 57.539 |
| 48 | 673.637 | 557.190 | 644.156 | 624.994 | 60.542 |
| 54 | 710.424 | 589.928 | 673.732 | 658.028 | 61.764 |
| 72 | 775.731 | 658.875 | 730.494 | 721.700 | 58.922 |
| 78 | 797.630 | 683.131 | 750.651 | 743.804 | 57.556 |
| 96 | 849.997 | 740.000 | 798.214 | 796.070 | 55.030 |
| 102 | 869.626 | 760.343 | 816.749 | 815.573 | 54.651 |
| 120 | 920.773 | 815.518 | 863.640 | 866.644 | 52.692 |
| 144 | 989.349 | 893.304 | 927.645 | 936.766 | 48.668 |
| 168 | 1051.437 | 959.128 | 984.684 | 998.416 | 47.652 |

Based on the permeation results of Example 3, listed in Table 3B, the following flux results listed in Table 3C below were obtained:

TABLE 3C

| | μg/cm²/hr | | | | |
| --- | --- | --- | --- | --- | --- |
| Hours | Test 3-1 | Test 3-2 | Test 3-3 | Average of all 3 tests | STD DEV |
| 6 | 28.232 | 22.936 | 28.585 | 26.585 | 3.165 |
| 24 | 19.959 | 16.093 | 19.402 | 18.485 | 2.090 |
| 30 | 18.495 | 14.919 | 17.909 | 17.107 | 1.918 |
| 48 | 14.034 | 11.608 | 13.420 | 13.021 | 1.261 |
| 54 | 13.156 | 10.925 | 12.477 | 12.186 | 1.144 |
| 72 | 10.774 | 9.151 | 10.146 | 10.024 | 0.818 |
| 78 | 10.226 | 8.758 | 9.624 | 9.536 | 0.738 |
| 96 | 8.854 | 7.708 | 8.315 | 8.292 | 0.573 |
| 102 | 8.526 | 7.454 | 8.007 | 7.996 | 0.536 |
| 120 | 7.673 | 6.796 | 7.197 | 7.222 | 0.439 |
| 144 | 6.870 | 6.204 | 6.442 | 6.505 | 0.338 |
| 168 | 6.259 | 5.709 | 5.861 | 5.943 | 0.284 |
| $F_{6-168}$ | 4.577 | 4.447 | 4.171 | 4.398 | 0.208 |
| CORR | 0.927 | 0.955 | 0.924 | 0.936 | |
| $F_{48-168}$ | 3.076 | 3.309 | 2.794 | 3.060 | 0.258 |

EXAMPLE 4

A Felodipine reservoir and adhesive formulation was prepared having the formulation set forth in Table 4A below:

TABLE 4A

| Ingredient | Amount (gm) |
| --- | --- |
| Felodipine | 0.17 |
| Ethanol | 10.9 (95%) |
| Water | 13.4 |
| Klucel HF (enhancer/gelling agent) | 0.50 |
| Total | 25.0 |
| Polyethylene membrane | |
| Silicone adhesive | |

The formulation of Example 4 was prepared and incorporated into a permeation testing apparatus according to the same procedure as in Example 1, using Klucel HF as a gelling agent/enhancer.

The formulation of Example 4 was tested as in Example 1. Sample size and HPLC conditions were the same as in Example 1. Three replicate tests were conducted as in Example 1 (4-1, 4-2, 4-3) were conducted giving the results listed in Table 4B below:

TABLE 4B

| | μg/cm² | | | | |
| --- | --- | --- | --- | --- | --- |
| Hours | Test 4-1 | Test 4-1 | Test 4-3 | Average of all 3 tests | Std Dev |
| 6 | 40.368 | 63.676 | 97.437 | 67.160 | 28.694 |
| 24 | 132.406 | 165.607 | 235.124 | 177.712 | 52.418 |
| 30 | 143.927 | 188.622 | 252.759 | 195.103 | 54.705 |
| 48 | 185.019 | 249.691 | 310.949 | 248.553 | 62.973 |
| 54 | 196.244 | 272.670 | 323.827 | 264.247 | 64.207 |
| 72 | 232.750 | 325.489 | 382.304 | 313.514 | 75.493 |
| 78 | 241.331 | 338.190 | 391.950 | 323.824 | 76.330 |
| 96 | 278.900 | 387.065 | 444.166 | 370.044 | 83.938 |
| 120 | 337.993 | 463.965 | 528.622 | 443.527 | 96.944 |
| 144 | 403.941 | 535.572 | 612.357 | 517.290 | 105.404 |
| 168 | 420.701 | 590.410 | 672.512 | 561.208 | 128.420 |

Based on the permeation results of Example 10, listed in Table 10B, the following flux results listed in Table 10C below were obtained:

TABLE 4C

| | μg/cm²/hr | | | | |
| --- | --- | --- | --- | --- | --- |
| Hours | Test 4-1 | Test 4-2 | Test 4-3 | Average of all 3 tests | STD DEV |
| 6 | 6.728 | 10.613 | 16.240 | 11.193 | 4.782 |
| 24 | 5.517 | 6.900 | 9.797 | 7.405 | 2.184 |
| 30 | 4.798 | 6.287 | 8.425 | 6.503 | 1.823 |
| 48 | 3.855 | 5.202 | 6.478 | 5.178 | 1.312 |
| 54 | 3.634 | 5.049 | 5.997 | 4.893 | 1.189 |
| 72 | 3.233 | 4.521 | 5.310 | 4.354 | 1.049 |
| 78 | 3.094 | 4.336 | 5.025 | 4.152 | 0.979 |
| 96 | 2.905 | 4.032 | 4.627 | 3.855 | 0.874 |
| 120 | 2.817 | 3.866 | 4.405 | 3.696 | 0.808 |
| 144 | 2.805 | 3.719 | 4.252 | 3.592 | 0.732 |
| 168 | 2.504 | 3.514 | 4.003 | 3.341 | 0.764 |
| $F_{6-168}$ | 2.247 | 3.111 | 3.286 | 2.882 | 0.556 |
| CORR | 0.990 | 0.994 | 0.991 | 0.993 | |
| $F_{48-168}$ | 2.097 | 2.864 | 3.092 | 2.685 | 0.521 |

EXAMPLE 5

A Felodipine reservoir and adhesive formulation was prepared having the formulation set forth in Table 5A below:

TABLE 5A

| Ingredient | Amount (gm) |
|---|---|
| Felodipine | 0.17 |
| Ethanol | 10.93 (95%) |
| Water | 13.4 |
| Klucel HF (enhancer/gelling agent) | 0.50 |
| Total | 25.0 |
| Polyethylene membrane | |
| Silicone adhesive | |

The formulation of Example 5 was prepared and incorporated into a permeation testing apparatus according to the same procedure as in Example 1.

The formulation of Example 5 was tested as in Example 1. Sample size and HPLC conditions were the same as in Example 1. Three replicate tests were conducted as in Example 1 (5-1, 5-2, 5-3) were conducted giving the results listed in Table 5B below:

TABLE 5B

| | μg/cm² | | | | |
|---|---|---|---|---|---|
| Hours | Test 5-1 | Test 5-2 | Test 5-3 | Average of all 3 tests | Std Dev |
| 6 | 108.929 | 102.945 | 78.883 | 96.920 | 15.904 |
| 24 | 313.118 | 279.095 | 234.543 | 275.585 | 39.405 |
| 30 | 348.029 | 308.172 | 262.911 | 306.371 | 42.588 |
| 48 | 447.447 | 417.596 | 349.656 | 404.900 | 50.117 |
| 54 | 469.616 | 458.469 | 386.127 | 438.071 | 45.328 |
| 72 | 552.474 | 549.480 | 449.686 | 517.213 | 58.500 |
| 78 | 569.641 | 557.283 | 459.007 | 528.644 | 60.623 |
| 96 | 641.635 | 631.581 | 523.665 | 598.960 | 65.401 |
| 120 | 727.598 | 722.084 | 609.134 | 686.272 | 66.860 |
| 144 | 790.178 | 801.927 | 685.602 | 759.236 | 64.039 |
| 168 | 828.213 | 865.658 | 752.954 | 815.608 | 57.400 |

Based on the permeation results of Example 5, listed in Table 5B, the following flux results listed in Table 5C below were obtained:

TABLE 5C

| | μg/cm²/hr | | | | |
|---|---|---|---|---|---|
| Hours | Test 5-1 | Test 5-2 | Test 5-3 | Average of all 3 tests | STD DEV |
| 6 | 18.155 | 17.158 | 13.147 | 16.153 | 2.651 |
| 24 | 13.047 | 11.629 | 9.773 | 11.483 | 1.642 |
| 30 | 11.601 | 10.272 | 8.764 | 10.212 | 1.420 |
| 48 | 9.322 | 8.700 | 7.285 | 8.435 | 1.044 |
| 54 | 8.697 | 8.490 | 7.151 | 8.112 | 0.839 |
| 72 | 7.673 | 7.632 | 6.246 | 7.184 | 0.812 |
| 78 | 7.303 | 7.145 | 5.885 | 6.777 | 0.777 |
| 96 | 6.684 | 6.579 | 5.455 | 6.239 | 0.681 |
| 120 | 6.063 | 6.017 | 5.076 | 5.719 | 0.557 |
| 144 | 5.487 | 5.569 | 4.761 | 5.272 | 0.445 |
| 168 | 4.930 | 5.153 | 4.482 | 4.855 | 0.342 |
| $F_{6-168}$ | 4.117 | 4.455 | 3.876 | 4.149 | 0.291 |

TABLE 5C-continued

| | μg/cm²/hr | | | | |
|---|---|---|---|---|---|
| Hours | Test 5-1 | Test 5-2 | Test 5-3 | Average of all 3 tests | STD DEV |
| CORR | 0.968 | 0.961 | 0.985 | 0.979 | |
| $F_{48-168}$ | 3.286 | 3.698 | 3.332 | 3.439 | 0.226 |

EXAMPLE 6

A Felodipine active drug/adhesive matrix formulation was prepared having the formulation set forth in Table 6A below:

TABLE 6A

| Ingredient | Amount (gm) |
|---|---|
| Felodipine | 0.4 |
| Ethyl acetate | 1.6 |
| BIO PSA 7-4302 (adhesive solution) containing 9.6 gm silicone adhesive (60% solids) | 16 |
| Total | 18 |

The formulation of Table 6A was prepared and incorporated into a permeation testing apparatus according to the following procedure:

1. Felodipine is dispersed in the requisite amount of ethyl acetate and adhesive solution to make the active drug/adhesive matrix.
2. The active drug/adhesive matrix is applied to a backing layer and dried.
3. The formulation is then applied to the human cadaver skin affixed to the receptor cell.

The formulation of Example 6 was tested using a permeation cell with a definable surface area for permeation. The receptor of the permeation cell was Ethanol:water (40:60) and the test substrate through which transdermal delivery was sought was human cadaver skin. Samples of 1.0 ml were taken at time intervals set out in Table 6B. These samples were tested for felodipine concentration using high performance liquid chromatography (HPLC). The HPLC conditions for determination of drug concentration are set forth below:

HPLC conditions for determination of felodipine concentration.

| | |
|---|---|
| Column | Hypersil C18, 5 μm, 4.6 mm × 25 cm |
| Mobile phase | Acetonitrile/Buffer 70/30 |
| Buffer: | 0.01M phosphate @ pH 4.5 |
| Flow rate | 1 ml/min |
| UV detection | 237 nm |
| Injection volume | 20 microl |
| Retention time | 5.0 min |

Three replicate tests (6-1, 6-2, 6-3) were conducted giving the results listed in Table 6B below:

TABLE 6B

| Test # | Sampling Time (Hours) | Drug Conc. (µg/ml) | Receptor Volume (ml) | Drug Amount (µg) | Sampling Volume (ml) | Drug Loss due to Sampling (µg) | Cumulative Drug Loss (µg) | Cumulative Amount Permeated (µg) | Amount Permeated per $cm^2$ (µg/$cm^2$) |
|---|---|---|---|---|---|---|---|---|---|
| 6-1 | 4 | 1.239 | 13 | 16.107 | 1 | 1.239 | 0.000 | 16.107 | 9.115 |
| | 24 | 17.305 | 13 | 224.965 | 1 | 17.305 | 1.239 | 226.204 | 128.016 |
| | 28 | 18.888 | 13 | 245.544 | 1 | 18.888 | 18.544 | 264.088 | 149.456 |
| | 48 | 31.875 | 13 | 414.375 | 1 | 31.875 | 37.432 | 451.807 | 255.692 |
| | 52 | 31.676 | 13 | 411.788 | 1 | 31.676 | 69.307 | 481.095 | 272.267 |
| | 72 | 42.285 | 13 | 549.705 | 1 | 42.285 | 100.983 | 650.688 | 368.244 |
| | 76 | 40.663 | 13 | 528.619 | 1 | 40.663 | 143.268 | 671.887 | 380.242 |
| | 96 | 49.885 | 13 | 648.505 | 1 | 49.885 | 183.931 | 832.436 | 471.101 |
| 6-2 | 4 | 1.496 | 13 | 19.448 | 1 | 1.496 | 0.000 | 19.448 | 11.006 |
| | 24 | 17.102 | 13 | 222.326 | 1 | 17.102 | 1.496 | 223.822 | 126.668 |
| | 28 | 18.597 | 13 | 241.761 | 1 | 18.597 | 18.598 | 260.359 | 147.345 |
| | 48 | 30.864 | 13 | 401.232 | 1 | 30.864 | 37.195 | 438.427 | 248.119 |
| | 52 | 30.158 | 13 | 392.054 | 1 | 30.158 | 68.059 | 460.113 | 260.392 |
| | 72 | 39.394 | 13 | 512.122 | 1 | 39.394 | 98.217 | 610.339 | 345.410 |
| | 76 | 37.508 | 13 | 487.604 | 1 | 37.508 | 137.611 | 625.215 | 353.829 |
| | 96 | 45.719 | 13 | 594.347 | 1 | 45.719 | 175.119 | 769.466 | 435.465 |
| 6-3 | 4 | 1.649 | 13 | 21.437 | 1 | 1.649 | 0.000 | 21.437 | 12.132 |
| | 24 | 17.004 | 13 | 221.052 | 1 | 17.004 | 1.649 | 222.701 | 126.033 |
| | 28 | 18.247 | 13 | 237.211 | 1 | 18.247 | 18.653 | 255.864 | 144.801 |
| | 48 | 30.048 | 13 | 390.624 | 1 | 30.048 | 36.900 | 427.524 | 241.949 |
| | 52 | 30.057 | 13 | 390.741 | 1 | 30.057 | 66.948 | 457.689 | 259.020 |
| | 72 | 39.708 | 13 | 516.204 | 1 | 39.708 | 97.005 | 613.209 | 347.034 |
| | 76 | 38.521 | 13 | 500.773 | 1 | 38.521 | 136.713 | 637.486 | 360.773 |
| | 96 | 46.559 | 13 | 605.267 | 1 | 46.559 | 175.234 | 780.501 | 441.710 |

Based on the permeation results of Example 6, listed in Table 6B, the averages of all three tests were calculated and the flux results listed in Table 6C below were obtained:

TABLE 6C

| | µg/$cm^2$ | | | | | µg/$cm^2$/ |
|---|---|---|---|---|---|---|
| Hours | 6-1 | 6-2 | 6-3 | Average of all 3 tests | Std Dev | hr |
| 4 | 9.115 | 11.006 | 12.132 | 10.751 | 1.525 | 2.688 |
| 24 | 128.016 | 126.668 | 126.033 | 126.906 | 1.013 | 5.288 |
| 28 | 149.456 | 147.345 | 144.801 | 147.201 | 2.331 | 5.257 |
| 48 | 255.692 | 248.119 | 241.949 | 248.587 | 6.883 | 5.179 |
| 52 | 272.267 | 260.392 | 259.020 | 263.893 | 7.284 | 5.075 |
| 72 | 368.244 | 345.410 | 347.034 | 353.563 | 12.740 | 4.911 |
| 76 | 380.242 | 353.829 | 360.773 | 364.948 | 13.693 | 4.802 |
| 96 | 471.101 | 435.465 | 441.710 | 449.425 | 19.030 | 4.682 |
| $F_{4-96}$ | 4.978 | 4.545 | 4.626 | 4.716 | 0.230 | |
| CORR | 0.998 | 0.996 | 0.998 | 0.997 | | |

EXAMPLE 7

A Felodipine active drug/adhesive matrix formulation was prepared having the formulation set forth in Table 7A below:

TABLE 7A

| Ingredient | Amount (gm) |
|---|---|
| Felodipine | 0.23 |
| Ethyl acetate | 0.89 |
| BIO PSA 7-4302 (adhesive solution) containing 12.4 gm silicone adhesive (60% solids) | 20.6 |
| Total | 21.72 |

The formulation of Example 7 was prepared and incorporated into a permeation testing apparatus according to the same procedure as in Example 6.

The formulation of Example 7 was tested as in Example 6. Sample size and HPLC conditions were the same as in Example 6. Three replicate tests were conducted as in Example 1 (7-1, 7-2, 7-3) giving the results listed in Table 7B below:

TABLE 7B

| | µg/$cm^2$ | | | | |
|---|---|---|---|---|---|
| Hours | Test 7-1 | Test 7-2 | Test 7-3 | Average of all 3 tests | Std Dev |
| 4 | 26.875 | 19.504 | 21.409 | 22.596 | 3.826 |
| 24 | 209.015 | 157.684 | 169.624 | 178.774 | 26.861 |
| 28 | 241.274 | 173.509 | 189.550 | 201.444 | 35.414 |
| 48 | 326.658 | 260.359 | 280.237 | 289.085 | 34.024 |
| 52 | 356.100 | 276.127 | 295.224 | 309.150 | 41.766 |
| 72 | 405.952 | 326.666 | 342.315 | 358.311 | 41.994 |
| 76 | 424.112 | 343.125 | 357.132 | 374.790 | 43.285 |
| 96 | 454.743 | 376.769 | 382.102 | 404.538 | 43.560 |
| 120 | 514.126 | 444.969 | 445.265 | 468.120 | 39.843 |
| 144 | 545.256 | 491.092 | 476.237 | 504.195 | 36.327 |
| 168 | 570.977 | 526.639 | 502.035 | 533.217 | 34.939 |

Based on the permeation results of Example 7, listed in Table 7B, the averages of all three tests were calculated and the flux results listed in Table 7C below were obtained:

TABLE 7C

| | µg/$cm^2$/hr | | | | |
|---|---|---|---|---|---|
| Hours | Test 7-1 | Test 7-2 | Test 7-3 | Average of all 3 tests | STD DEV |
| 4 | 6.719 | 4.876 | 5.352 | 5.649 | 0.957 |
| 24 | 8.709 | 6.570 | 7.068 | 7.449 | 1.119 |
| 28 | 8.617 | 6.197 | 6.770 | 7.194 | 1.265 |

TABLE 7C-continued

| | | | µg/cm²/hr | | |
|---|---|---|---|---|---|
| Hours | Test 7-1 | Test 7-2 | Test 7-3 | Average of all 3 tests | STD DEV |
| 48 | 6.805 | 5.424 | 5.838 | 6.023 | 0.709 |
| 52 | 6.848 | 5.310 | 5.677 | 5.945 | 0.803 |
| 72 | 5.638 | 4.537 | 4.754 | 4.977 | 0.583 |
| 76 | 5.580 | 4.515 | 4.699 | 4.931 | 0.570 |
| 96 | 4.737 | 3.925 | 3.980 | 4.214 | 0.454 |
| 120 | 4.284 | 3.708 | 3.711 | 3.901 | 0.332 |
| 144 | 3.787 | 3.410 | 3.307 | 3.501 | 0.252 |
| 168 | 3.399 | 3.135 | 2.988 | 3.174 | 0.208 |
| $F_{4-168}$ | 2.931 | 2.854 | 2.642 | 2.809 | 0.150 |
| CORR | 0.934 | 0.970 | 0.948 | 0.952 | |

EXAMPLE 8

A Felodipine active drug/adhesive matrix formulation was prepared having the formulation set forth in Table 8A below:

TABLE 8A

| Ingredient | Amount (gm) |
|---|---|
| Felodipine | 0.46 |
| Ethyl acetate | 1.78 |
| BIO PSA 7-4302 (adhesive solution) containing 11.5 gm silicone adhesive (60% solids) | 19.2 |
| Total | 21.44 |

The formulation of Example 8 was prepared and incorporated into a permeation testing apparatus according to the same procedure as in Example 6.

The formulation of Example 8 was tested as in Example 6. Sample size and HPLC conditions were the as in Example 6. Three replicate tests were conducted as in Example 6 (8-1, 8-2, 8-3) giving the results listed in Table 8B below:

TABLE 8B

| | | | µg/cm² | | |
|---|---|---|---|---|---|
| Hours | Test 8-1 | Test 8-2 | Test 8-3 | Average of all 3 tests | Std Dev |
| 4 | 18.349 | 23.374 | 47.954 | 29.892 | 15.842 |
| 24 | 192.718 | 207.370 | 308.729 | 236.272 | 63.176 |
| 28 | 225.636 | 232.085 | 335.990 | 264.570 | 61.935 |
| 48 | 325.358 | 345.351 | 487.377 | 386.029 | 88.338 |
| 52 | 346.537 | 374.671 | 517.759 | 412.989 | 91.817 |
| 72 | 404.506 | 434.863 | 599.225 | 479.531 | 104.763 |
| 76 | 418.675 | 456.259 | 620.123 | 498.352 | 107.118 |
| 96 | 459.932 | 499.242 | 653.037 | 537.404 | 102.052 |
| 120 | 537.091 | 560.783 | 730.431 | 609.435 | 105.453 |
| 144 | 584.445 | 602.545 | 777.568 | 654.853 | 106.659 |
| 168 | 624.448 | 641.538 | 811.649 | 692.545 | 103.500 |

Based on the permeation results of Example 8, listed in Table 8B, the averages of all three tests were calculated and the flux results listed in Table 8C below were obtained:

TABLE 8C

| | | | µg/cm²/hr | | |
|---|---|---|---|---|---|
| Hours | Test 8-1 | Test 8-2 | Test 8-3 | Average of all 3 tests | STD DEV |
| 4 | 4.587 | 5.844 | 11.989 | 7.473 | 3.961 |
| 24 | 8.030 | 8.640 | 12.864 | 9.845 | 2.632 |
| 28 | 8.058 | 8.289 | 12.000 | 9.449 | 2.212 |
| 48 | 6.778 | 7.195 | 10.154 | 8.042 | 1.840 |
| 52 | 6.664 | 7.205 | 9.957 | 7.942 | 1.766 |
| 72 | 5.618 | 6.040 | 8.323 | 6.660 | 1.455 |
| 76 | 5.509 | 6.003 | 8.160 | 6.557 | 1.409 |
| 96 | 4.791 | 5.200 | 6.802 | 5.598 | 1.063 |
| 120 | 4.476 | 4.673 | 6.087 | 5.079 | 0.879 |
| 144 | 4.059 | 4.184 | 5.400 | 4.548 | 0.741 |
| 168 | 3.717 | 3.819 | 4.831 | 4.122 | 0.616 |
| $F_{4-168}$ | 3.346 | 3.417 | 4.105 | 3.623 | 0.419 |
| CORR | 0.959 | 0.949 | 0.927 | 0.944 | |

EXAMPLE 9

A Felodipine active drug/adhesive matrix formulation was prepared having the formulation set forth in Table 9A below:

TABLE 9A

| Ingredient | Amount (gm) |
|---|---|
| Felodipine | 0.70 |
| Ethyl acetate | 2.67 |
| BIO PSA 7-4302 (adhesive solution) containing 10.7 gm silicone adhesive (60% solids) | 17.8 |
| Total | 21.17 |

The formulation of Example 9 was prepared and incorporated into a permeation testing apparatus according to the same procedure as in Example 6.

The formulation of Example 9 was tested as in Example 6. Sample size and HPLC conditions were the same as in Example 6. Three replicate tests were conducted as in Example 6 (9-1, 9-2, 9-3) giving the results listed in Table 9B below:

TABLE 9B

| | | | µg/cm² | | |
|---|---|---|---|---|---|
| Hours | Test 9-1 | Test 9-2 | Test 9-3 | Average of all 3 tests | Std Dev |
| 4 | 16.524 | 37.455 | 36.918 | 30.299 | 11.933 |
| 24 | 205.379 | 314.447 | 301.913 | 273.913 | 59.682 |
| 28 | 232.196 | 356.446 | 338.405 | 309.016 | 67.137 |
| 48 | 337.964 | 479.965 | 484.818 | 434.249 | 83.421 |
| 52 | 362.508 | 525.171 | 529.111 | 472.263 | 95.071 |
| 72 | 415.780 | 600.848 | 613.187 | 543.272 | 110.583 |
| 76 | 430.774 | 633.583 | 667.014 | 577.124 | 127.840 |
| 96 | 468.083 | 673.445 | 704.399 | 615.309 | 128.437 |
| 120 | 549.756 | 778.694 | 806.885 | 711.778 | 141.022 |
| 144 | 609.880 | 840.617 | 884.202 | 778.233 | 147.418 |
| 168 | 659.291 | 902.965 | 939.035 | 833.764 | 152.170 |

Based on the permeation results of Example 9, listed in Table 9B, the averages of all three tests were calculated and the flux results listed in Table 9C below were obtained:

TABLE 9C

| | $\mu g/cm^2/hr$ | | | | |
|---|---|---|---|---|---|
| Hours | Test 9-1 | Test 9-2 | Test 9-3 | Average of all 3 tests | STD DEV |
| 4 | 4.131 | 9.364 | 9.230 | 7.575 | 2.983 |
| 24 | 8.557 | 13.102 | 12.580 | 11.413 | 2.487 |
| 28 | 8.293 | 12.730 | 12.086 | 11.036 | 2.398 |
| 48 | 7.041 | 9.999 | 10.100 | 9.047 | 1.738 |
| 52 | 6.971 | 10.099 | 10.175 | 9.082 | 1.828 |
| 72 | 5.775 | 8.345 | 8.516 | 7.545 | 1.536 |
| 76 | 5.668 | 8.337 | 8.777 | 7.594 | 1.682 |
| 96 | 4.876 | 7.015 | 7.337 | 6.409 | 1.338 |
| 120 | 4.581 | 6.489 | 6.724 | 5.931 | 1.175 |
| 144 | 4.235 | 5.838 | 6.140 | 5.404 | 1.024 |
| 168 | 3.924 | 5.375 | 5.589 | 4.963 | 0.906 |
| $F_{4-168}$ | 3.497 | 4.653 | 5.004 | 4.385 | 0.789 |
| CORR | 0.962 | 0.951 | 0.956 | 0.956 | |

EXAMPLE 10 (42)

A Felodipine active drug/adhesive matrix formulation was prepared having the formulation set forth in Table 10A below:

TABLE 10A

| Ingredient | Amount (gm) |
|---|---|
| Felodipine | 0.4 |
| Ethyl acetate | 1.5 |
| BIO PSA 7-4302 (adhesive solution) containing 18.6 gm silicone adhesive (60% solids) | 31.0 |
| Total | 32.9 |

The formulation of Example 10 was prepared and incorporated into a permeation testing apparatus according to the same procedure as in Example 6.

The formulation of Example 10 was tested as in Example 6. Sample size and HPLC conditions were the same as in Example 6. Three replicate tests were conducted as in Example 6 (10-1, 10-2, 10-3) giving the results listed in Table 10B below:

TABLE 10B

| | $\mu g/cm^2$ | | | | |
|---|---|---|---|---|---|
| Hours | Test 10-1 | Test 10-2 | Test 10-3 | Average of all 3 tests | Std Dev |
| 6 | 40.068 | 76.197 | 35.599 | 50.621 | 22.262 |
| 24 | 251.407 | 331.110 | 241.432 | 274.650 | 49.150 |
| 30 | 293.227 | 380.646 | 279.694 | 317.856 | 54.797 |
| 48 | 376.524 | 470.580 | 355.225 | 400.776 | 61.383 |
| 54 | 405.810 | 501.570 | 388.094 | 431.825 | 61.047 |
| 72 | 459.156 | 568.308 | 439.166 | 488.883 | 69.505 |
| 78 | 479.973 | 592.938 | 463.962 | 512.291 | 70.300 |
| 96 | 525.231 | 642.425 | 504.857 | 557.504 | 74.246 |
| 102 | 540.975 | 667.262 | 521.104 | 576.447 | 79.273 |
| 120 | 574.084 | 698.860 | 550.553 | 607.832 | 79.705 |
| 144 | 612.784 | 744.643 | 584.507 | 647.311 | 85.469 |
| 168 | 657.051 | 798.065 | 631.916 | 695.677 | 89.557 |

Based on the permeation results of Example 10, listed in Table 10B, the averages of all three were calculated and the flux results listed in Table 10C below were obtained:

TABLE 10C

| | $\mu g/cm^2/hr$ | | | | |
|---|---|---|---|---|---|
| Hours | Test 10-1 | Test 10-2 | Test 10-3 | Average of all 3 tests | STD DEV |
| 6 | 6.678 | 12.700 | 5.933 | 8.437 | 3.710 |
| 24 | 10.475 | 13.796 | 10.060 | 11.444 | 2.048 |
| 30 | 9.774 | 12.688 | 9.323 | 10.595 | 1.827 |
| 48 | 7.844 | 9.804 | 7.401 | 8.350 | 1.279 |
| 54 | 7.515 | 9.288 | 7.187 | 7.997 | 1.131 |
| 72 | 6.377 | 7.893 | 6.100 | 6.790 | 0.965 |
| 78 | 6.154 | 7.602 | 5.948 | 6.568 | 0.901 |
| 96 | 5.471 | 6.692 | 5.259 | 5.807 | 0.773 |
| 102 | 5.304 | 6.542 | 5.109 | 5.651 | 0.777 |
| 120 | 4.784 | 5.824 | 4.588 | 5.065 | 0.664 |
| 144 | 4.255 | 5.171 | 4.059 | 4.495 | 0.594 |
| 168 | 3.911 | 4.750 | 3.761 | 4.141 | 0.533 |
| $F_{6-168}$ | 3.299 | 3.827 | 3.183 | 3.436 | 0.343 |
| CORR | 0.935 | 0.933 | 0.935 | 0.935 | |

EXAMPLE 11

A Felodipine active drug/adhesive matrix formulation was prepared having the formulation set forth in Table 11A below:

TABLE 11A

| Ingredient | Amount (gm) |
|---|---|
| Felodipine | 0.4 |
| Ethyl acetate | 1.5 |
| BIO PSA 7-4302 (adhesive solution) containing 18.6 gm silicone adhesive (60% solids) | 31.0 |
| Total | 32.9 |

The formulation of Example 11 was prepared and incorporated into a permeation testing apparatus according to the same procedure as in Example 6.

The formulation of Example 11 was tested as in Example 6. Sample size and HPLC conditions were the same as in Example 6. Three replicate tests were conducted as in Example 6 (11-1, 11-2, 11-3) giving the results listed in Table 11B below:

TABLE 11B

| | $\mu g/cm^2$ | | | | |
|---|---|---|---|---|---|
| Hours | Test 11-1 | Test 11-2 | Test 11-3 | Average of all 3 tests | Std Dev |
| 6 | 68.937 | 58.295 | 70.662 | 65.965 | 6.698 |
| 24 | 263.402 | 269.001 | 290.024 | 274.142 | 14.036 |
| 30 | 295.223 | 307.997 | 322.300 | 308.507 | 13.546 |
| 48 | 352.382 | 370.535 | 377.866 | 366.928 | 13.119 |
| 54 | 378.195 | 391.252 | 392.165 | 387.204 | 7.815 |
| 72 | 423.208 | 431.628 | 432.850 | 429.229 | 5.250 |
| 78 | 443.895 | 448.411 | 452.170 | 448.159 | 4.143 |
| 96 | 480.775 | 476.123 | 486.720 | 481.206 | 5.312 |
| 102 | 497.597 | 488.703 | 493.466 | 493.255 | 4.451 |
| 120 | 528.767 | 511.241 | 524.125 | 521.378 | 9.080 |
| 144 | 568.225 | 537.408 | 554.291 | 553.308 | 15.432 |
| 168 | 626.550 | 576.344 | 603.543 | 602.146 | 25.132 |

Based on the permeation results of Example 11, listed in Table 11B, the averages of all three tests were calculated and the flux results listed in Table 11C below were obtained:

TABLE 11C

| | μg/cm$^2$/hr | | | | |
|---|---|---|---|---|---|
| Hours | Test 11-1 | Test 11-2 | Test 11-3 | Average of all 3 tests | STD DEV |
| 6 | 11.490 | 9.716 | 11.777 | 10.994 | 1.116 |
| 24 | 10.975 | 11.208 | 12.084 | 11.423 | 0.585 |
| 30 | 9.841 | 10.267 | 10.743 | 10.284 | 0.452 |
| 48 | 7.341 | 7.719 | 7.872 | 7.644 | 0.273 |
| 54 | 7.004 | 7.245 | 7.262 | 7.170 | 0.145 |
| 72 | 5.878 | 5.995 | 6.012 | 5.962 | 0.073 |
| 78 | 5.691 | 5.749 | 5.797 | 5.746 | 0.053 |
| 96 | 5.008 | 4.960 | 5.070 | 5.013 | 0.055 |
| 102 | 4.878 | 4.791 | 4.838 | 4.836 | 0.044 |

TABLE 11C-continued

| | μg/cm$^2$/hr | | | | |
|---|---|---|---|---|---|
| Hours | Test 11-1 | Test 11-2 | Test 11-3 | Average of all 3 tests | STD DEV |
| 120 | 4.406 | 4.260 | 4.368 | 4.345 | 0.076 |
| 144 | 3.946 | 3.732 | 3.849 | 3.842 | 0.107 |
| 168 | 3.729 | 3.431 | 3.593 | 3.584 | 0.150 |
| $F_{6-168}$ | 2.911 | 2.592 | 2.643 | 2.715 | 0.171 |
| CORR | 0.947 | 0.904 | 0.917 | 0.925 | |

EXAMPLE 12

A Felodipine active drug/adhesive matrix formulation was prepared having the formulation set forth in Table 12A below:

TABLE 12A

| Ingredient | Amount (gm) |
|---|---|
| Felodipine | 0.4 |
| Ethyl acetate | 1.6 |
| DURO-TAK 87-4098 (adhesive solution) containing 9.6 gm acrylate adhesive (38.5% solids) | 24.0 |
| Total | 26.0 |

The formulation of Example 12 was prepared and incorporated into a permeation testing apparatus according to the same procedure as in Example 6.

Three permeation tests (12-1, 12-2, 12-3) were conducted giving the results listed in Table 12B below:

TABLE 12B

| Test # | Sampling Time (Hours) | Drug Conc. (μg/ml) | Receptor Volume (ml) | Drug Amount (μg) | Sampling Volume (ml) | Drug Loss due to Sampling (μg) | Cumulative Drug Loss (μg) | Cumulative Amount Permeated (μg) | Amount Permeated per cm$^2$ (μg/cm$^2$) |
|---|---|---|---|---|---|---|---|---|---|
| 12-1 | 4 | 0.000 | 13 | 0 | 1 | 0.000 | 0.000 | 0.000 | 0.000 |
| | 24 | 3.233 | 13 | 42.029 | 1 | 3.233 | 0.000 | 42.029 | 23.786 |
| | 28 | 3.623 | 13 | 47.099 | 1 | 3.623 | 3.233 | 50.332 | 28.484 |
| | 48 | 6.601 | 13 | 85.813 | 1 | 6.601 | 6.856 | 92.669 | 52.444 |
| | 52 | 6.694 | 13 | 87.022 | 1 | 6.694 | 13.457 | 100.479 | 56.864 |
| | 72 | 9.825 | 13 | 127.725 | 1 | 9.825 | 20.151 | 147.876 | 83.688 |
| | 76 | 9.631 | 13 | 125.203 | 1 | 9.631 | 29.976 | 155.179 | 87.821 |
| | 96 | 12.587 | 13 | 163.631 | 1 | 12.587 | 39.607 | 203.238 | 115.019 |
| 12-2 | 4 | 0.000 | 13 | 0 | 1 | 0.000 | 0.000 | 0.000 | 0.000 |
| | 24 | 2.486 | 13 | 32.318 | 1 | 0.000 | 0.000 | 32.318 | 18.290 |
| | 28 | 2.775 | 13 | 36.075 | 1 | 2.486 | 2.486 | 38.561 | 21.823 |
| | 48 | 5.056 | 13 | 65.728 | 1 | 5.261 | 5.261 | 70.989 | 40.175 |
| | 52 | 5.152 | 13 | 66.976 | 1 | 10.317 | 10.317 | 77.293 | 43.743 |
| | 72 | 7.270 | 13 | 94.51 | 1 | 15.469 | 15.469 | 109.979 | 62.241 |
| | 76 | 7.171 | 13 | 93.223 | 1 | 22.739 | 22.739 | 115.962 | 65.626 |
| | 96 | 8.958 | 13 | 116.454 | 1 | 29.910 | 29.910 | 146.364 | 82.832 |
| 12-3 | 4 | 0.000 | 13 | 0 | 1 | 0.000 | 0.000 | 0.000 | 0.000 |
| | 24 | 3.603 | 13 | 46.839 | 1 | 0.000 | 0.000 | 46.839 | 26.508 |
| | 28 | 4.013 | 13 | 52.169 | 1 | .3603 | 3.603 | 55.772 | 31.563 |
| | 48 | 7.395 | 13 | 96.135 | 1 | 7.616 | 7.616 | 103.751 | 58.716 |
| | 52 | 7.389 | 13 | 96.057 | 1 | 15.011 | 15.011 | 111.068 | 62.857 |
| | 72 | 10.193 | 13 | 132.509 | 1 | 22.400 | 22.400 | 154.909 | 87.668 |
| | 76 | 9.894 | 13 | 128.622 | 1 | 32.593 | 32.593 | 161.215 | 91.237 |
| | 96 | 12.507 | 13 | 162.591 | 1 | 42.487 | 42.487 | 205.078 | 116.060 |

Based on the permeation results of Example 12, listed in Table 12B, the averages of the three tests were calculated and the permeation results and mean flux rates between 4–96 hours ($F_{4-96}$) are listed in Table 12C below:

TABLE 12C

| | μg/cm$^2$ | | | | |
|---|---|---|---|---|---|
| Hours | Test 12-1 | Test 12-2 | Test 12-3 | Average of all 3 tests | STD DEV |
| 4 | 0.000 | 0.000 | 0.000 | 0.000 | 0.000 |
| 24 | 23.786 | 18.290 | 26.508 | 22.861 | 4.186 |
| 28 | 28.484 | 21.823 | 31.563 | 27.290 | 4.979 |
| 48 | 52.444 | 40.175 | 58.716 | 50.445 | 9.431 |
| 52 | 56.864 | 43.743 | 62.857 | 54.488 | 9.776 |
| 72 | 83.688 | 62.241 | 87.668 | 77.866 | 13.677 |
| 76 | 87.821 | 65.626 | 91.237 | 81.561 | 13.906 |
| 96 | 115.019 | 82.832 | 116.060 | 104.637 | 18.891 |
| $F_{4-96}$ | 1.247 | 0.905 | 1.260 | 1.137 | 0.201 |
| CORR | 1.000 | 1.000 | 1.000 | 1.000 | |

EXAMPLE 13

A Felodipine double active drug/adhesive matrix and membrane formulation was prepared having the formulation set forth in Table 13A below:

TABLE 13A

| Ingredient | Amount (gm) |
|---|---|
| MATRIX 1 | |
| Felodipine | 0.93 |
| Ethyl acetate | 3.56 |
| BIO PSA 7-4302 (adhesive solution) containing 10.6 gm silicone adhesive (60% solids) | 18.1 |
| Total | 22.59 |
| *Polyethylene membrane* | |
| MATRIX 2 | |
| Felodipine | 0.23 |
| Ethyl acetate | 0.89 |
| BIO PSA 7-4302 (adhesive solution) containing 12.4 gm silicone adhesive (60% solids) | 20.6 |
| Total | 21.72 |

The formulation of Example 13 was prepared and incorporated into a permeation testing apparatus according to the following procedure:

1. For each matrix layer, felodipine is mixed with the requisite amounts of ethyl acetate and adhesive solution to form the active drug/adhesive matrix.
2. Matrix formulation 1 is applied to the first side of the polyethylene membrane and matrix formulation 2 is applied to the opposite side of the membrane.
3. The formulation is then applied to the human cadaver skin affixed to the receptor cell.

The formulation of Example 13 was tested as in Example 6. Sample size and HPLC conditions were the same as in Example 6. Three replicate tests were conducted as in Example 1 (13-1, 13-2, 13-3) giving the results listed in Table 13B below:

TABLE 13B $\mu g/cm^2$

| Hours | Test 13-1 | Test 13-2 | Test 13-3 | Average of all 3 tests | Std Dev |
|---|---|---|---|---|---|
| 6 | 15.053 | 18.165 | 8.233 | 13.817 | 5.080 |
| 24 | 123.668 | 110.952 | 100.638 | 111.753 | 11.536 |
| 30 | 140.464 | 127.509 | 118.565 | 128.846 | 11.011 |
| 48 | 178.559 | 161.833 | 158.357 | 166.250 | 10.801 |
| 54 | 188.593 | 170.394 | 168.737 | 175.908 | 11.017 |
| 72 | 224.920 | 196.713 | 204.042 | 208.558 | 14.636 |
| 78 | 234.522 | 205.007 | 212.800 | 217.443 | 15.295 |
| 96 | 270.577 | 231.195 | 246.148 | 249.307 | 19.880 |
| 102 | 280.244 | 236.690 | 252.634 | 256.523 | 22.036 |
| 120 | 320.146 | 267.732 | 284.959 | 290.946 | 26.715 |
| 168 | 402.896 | 329.425 | 359.332 | 363.884 | 36.946 |

Based on the permeation results of Example 13, listed in Table 13B, the following flux results listed in Table 13C below were obtained:

TABLE 13C $\mu g/cm^2/hr$

| Hours | Test 13-1 | Test 13-2 | Test 13-3 | Average of all 3 tests | STD DEV |
|---|---|---|---|---|---|
| 6 | 2.509 | 3.028 | 1.372 | 2.303 | 0.847 |
| 24 | 5.153 | 4.623 | 4.193 | 4.656 | 0.481 |
| 30 | 4.682 | 4.250 | 3.952 | 4.295 | 0.367 |
| 48 | 3.720 | 3.372 | 3.299 | 3.464 | 0.225 |
| 54 | 3.492 | 3.155 | 3.125 | 3.258 | 0.204 |
| 72 | 3.124 | 2.732 | 2.834 | 2.897 | 0.203 |
| 78 | 3.007 | 2.628 | 2.728 | 2.788 | 0.196 |
| 96 | 2.819 | 2.408 | 2.564 | 2.597 | 0.207 |
| 102 | 2.747 | 2.320 | 2.477 | 2.515 | 0.216 |
| 120 | 2.668 | 2.231 | 2.375 | 2.425 | 0.223 |
| 168 | 2.398 | 1.961 | 2.139 | 2.166 | 0.220 |
| $F_{6-168}$ | 2.172 | 1.718 | 1.995 | 1.962 | 0.229 |
| CORR | 0.979 | 0.968 | 0.978 | 0.976 | |

It will be readily apparent that various modifications to the invention may be made by those skilled in the art without departing from the scope of this invention. For example, many different transdermal delivery systems may be utilized in order to obtain the relative release rates and plasma levels described herein. Further, it is possible that mean values for plasma concentration over a particular patient population for a particular described time point along the dosing interval may vary from the plasma concentration ranges described herein for that time point. Such obvious modifications are considered to be within the scope of the appended claims.

In vitro skin permeation studies with cadaver skin quantitatively predict the pharmacokinetics and extent of drug absorption from the transdermal delivery dosage form. Matching in vitro skin donors to the in vivo population improves the correlation. Further improvements in this correlation are achieved by matching application sites.

What is claimed is:

1. A method of effectively treating hypertension, angina, or both conditions in a human patient, comprising:
    administering felodipine transdermally to the human patient by applying a transdermal delivery system containing felodipine to the skin of a patient, and maintaining said transdermal delivery system in contact with the skin of said patient for at least 3 days, said transdermal delivery system maintaining an effective mean relative release rate to provide a therapeutic blood level of said felodipine within 36 hours from the initiation of the dosing interval, and thereafter maintaining a therapeutic blood level until the end of at least the three-day dosing interval.
    said transdermal delivery system having a mean relative release rate of from about 4.2 $\mu g/cm^2/hr$ to about 20.0 $\mu g/cm^2/hr$ at 24 hours;
    from about 3.3 $\mu g/cm^2/hr$ to about 14.0 $\mu g/cm^2/hr$ at 48 hours; and
    from about 2.7 $\mu tg/cm^2/hr$ to about 10.8 $\mu g/cm^2/hr$ at 72 hours; as determined via an in-vitro permeation test utilizing a Valia-Chien cell where the membrane is a human cadaver skin and said cell has a receptor chamber containing a 40:60 mixture of Ethanol:water;
    said transdermal delivery system providing a mean relative release rate of felodipine to provide a plasma level of felodipine of at least 0.1 ng/ml within about 6 hours after application of said transdermal delivery system onto the skin of said patient.

2. The method of claim 1, further comprising maintaining a plasma level of felodipine at steady-state from about 1.0 to about 3.0 ng/ml.

3. The method of claim 1, wherein said therapeutic plasma level is maintained from about 0.1 ng/ml to about 3.3 ng/ml during the dosing interval for said transdermal delivery system.

4. The method of claim 1, wherein said transdermal delivery system has a mean relative release rate from about 0.5 μm/hour/cm$^2$ to about 25 μm/hour/cm$^2$ of said transdermal delivery system.

5. The method of claim 1, wherein said transdermal delivery system provides an in-vitro cumulative amount of permeation of from about 63 μg/cm$^2$ to about 388 μg/cm$^2$ at 24 hours; from about 105 μg/cm$^2$ to about 660 μg/cm$^2$ at 48 hours; and from about 139 μg/cm$^2$ to about 854 μg/cm$^2$ at 72 hours, as determined via an in-vitro permeation test utilizing a Valia-Chien cell where the membrane is a human cadaver skin and said cell has a receptor chamber containing a 40:60 mixture of Ethanol:water.

6. The method of claim 1 wherein said transdermal delivery system is maintained in contact with the skin of the patient for at least 5 days, said transdermal delivery system maintaining an effective mean relative release rate to provide a therapeutic blood level of said felodipine within three days from the initiation of the dosing interval, and thereafter maintaining a therapeutic blood level until the end of at least the five-day dosing interval.

7. The method of claim 6, wherein the plasma level of felodipine at 48 hours does not decrease by more than 30% over the next 72 hours.

8. The method of claim 6, further comprising maintaining an effective mean relative release rate of said transdermal delivery system to provide a substantially first order plasma level increase of felodipine from the initiation of the dosing interval until about 48 to about 72 hours after the initiation of the dosing interval; and thereafter providing an effective mean relative release rate to provide a substantially zero order plasma level fluctuation of felodipine until the end of at least the five-day dosing interval.

9. The method of claim 6, further comprising maintaining a plasma level of felodipine at steady-state from about 1.5 to about 2.3 ng/ml.

10. The method of claim 6, wherein said therapeutic plasma level is maintained from about 0.1 ng/ml to about 3.3 ng/ml during the dosing interval for said transdermal delivery system.

11. The method of claim 6, wherein said transdermal delivery system has a mean relative release rate from about 0.5 μm/hour/cm$^2$ to about 25 μm/hour/cm$^2$ of said transdermal delivery system.

12. The method of claim 6, wherein said transdermal delivery system has a mean relative release rate of from about 2.4 μg/cm$^2$/hr to about 8.9 μg/cm$^2$/hr at 96 hours; as determined via an in-vitro permeation test utilizing a Valia-Chien cell where the membrane is a human cadaver skin and said cell has a receptor chamber containing a 40:60 mixture of Ethanol:water.

13. The method of claim 6, wherein said transdermal delivery system provides an in-vitro cumulative amount of permeation of from about 63 μg/cm$^2$ to about 388 μg/cm$^2$ at 24 hours; from about 105 μg/cm$^2$ to about 660 μg/cm$^2$ at 48 hours; and from about 139 μg/cm$^2$ to about 854 μg/cm$^2$ at 72 hours; and from about 231 μg/cm$^2$ to about 850 μg/cm$^2$ at 96 hours; as determined via an in-vitro permeation test utilizing a Valia-Chien cell where the membrane is a human cadaver skin and said cell has a receptor chamber containing a 40:60 mixture of Ethanol:water.

14. A transdermal delivery system containing felodipine or a pharmaceutically acceptable salt thereof which provides a mean relative release rate of from about 4.2 μg/cm$^2$/hr to about 20.0 μg/cm$^2$/hr at 24 hours;
   from about 3.3 μg/cm$^2$/hr to about 14.0 μg/cm$^2$/hr at 48 hours; and
   from about 2.7 μg/cm$^2$/hr to about 10.8 μg/cm$^2$/hr at 72 hours; as determined via an in-vitro permeation test utilizing a Valia-Chien cell where the membrane is a human cadaver skin and said cell has a receptor chamber containing a 40:60 mixture of ethanol:water;
   said transdermal delivery system providing a plasma level of felodipine of at least about 0.1 ng/ml by about 6 hours after application of said transdermal delivery system onto the skin of a human patient; said transdermal delivery system maintaining a therapeutic blood level until the end of at least a three-day dosing interval and said transdermal delivery system maintaining a plasma level of felodipine at steady-state from about 0.1 to about 3.3 ng/ml.

15. The transdermal delivery system of claim 14, which provides an in-vitro cumulative amount of permeation of from about 63 μg/cm$^2$ to about 388 μg/cm$^2$ at 24 hours; from about 105 μg/cm$^2$ to about 660 μg/cm$^2$ at 48 hours; and from about 139 μg/cm$^2$ to about 854 g/cm$^2$ at 72 hours; and from about 231 μg/cm$^2$ to about 850 μg/cm$^2$ at 96 hours; as determined via an in-vitro permeation test utilizing a Valia-Chien cell where the membrane is a human cadaver skin and said cell has a receptor chamber containing a 40:60 mixture of Ethanol:water.

16. The transdermal delivery system of claim 14, comprising a backing layer which is impermeable to the active substance, a pressure-sensitive adhesive reservoir layer, and optionally a removable protective layer, the reservoir layer by weight comprising 20 to 90% of a polymeric matrix, 0.1 to 30% of a softening agent, 0.1 to 20% of felodipine base or of a pharmaceutically acceptable salt thereof and 0.1 to 30% of a solvent for the felodipine or salt thereof.

17. The transdermal delivery system of claim 14, which is a laminated composite comprising (a) a polymer backing layer that is substantially impermeable to felodipine or the pharmaceutically acceptable salt thereof; and (b) a reservoir layer comprising an acrylate or silicon based pressure-sensitive adhesive, 0.1 to 20% of felodipine base or of a pharmaceutically acceptable salt thereof, 0.1 to 30% of an ester of a carboxylic acid acting as a softening agent and 0.1 to 30% of a solvent for felodipine having at least one acidic group.

18. The transdermal delivery system of claim 14, which maintains a plasma level of felodipine at steady-state from about 1.5 to about 2.3 ng/ml.

19. The transdermal delivery system of claim 14, wherein said transdermal delivery system maintains a therapeutic blood level until the end of at least a five-day dosing interval.

20. The transdermal delivery system of claim 19, which maintains a plasma level of felodipine at steady-state from about 1.5 to about 2.3 ng/ml.

21. The transdermal delivery system of claim 19, wherein said transdermal delivery system has a mean relative release rate from about 0.5 μm/hour/cm$^2$ to about 25 μm/hour/cm$^2$ of said transdermal delivery system.

22. The transdermal delivery system of claim 19, wherein said transdermal delivery system has a mean relative release rate from about 4.2 μg/cm$^2$/hr to about 20.0 μg/cm$^2$/hr at 24 hours; from about 3.3 µg/cm²/hr to about 14.0 µg/cm²/hr at 48 hours; and from about 2.7 µg/cm²/hr to about 10.8 µg/cm²/hr at 72 hours; and a mean relative release rate from about 2.4 µg/cm²/hr to about 8.9 µg/cm²/hr at 96 hours; as determined via an in-vitro permeation test utilizing a Valia-Chien cell where the membrane is a human cadaver skin and said cell has a receptor chamber containing a 40:60 mixture of Ethanol:water.

23. The transdermal delivery system of claim 19, wherein said transdermal delivery system provides an in-vitro cumulative amount of permeation of from about 63 µg/cm² to about 388 µg/cm² at 24 hours; from about 105 µg/cm² to about 660 µg/cm² at 48 hours; and from about 139 µg/cm² to about 854 µg/cm² at 72 hours; and from about 231 µg/cm² to about 850 µg/cm² at 96 hours; as determined via an in-vitro permeation test utilizing a Valia-Chien cell where the membrane is a human cadaver skin and said cell has a receptor chamber containing a 40:60 mixture of Ethanol:water.

24. The transdermal delivery system according to claim 16, wherein the backing layer is composed of a flexible material.

25. The transdermal delivery system according to claim 16, wherein the backing layer is selected from the group consisting of a flexible material, an inflexible material, and an aluminum foil.

26. The transdermal delivery system according to claim 16, wherein the polymeric matrix is at least one of rubber, a rubber-like synthetic homo-, co- or blockpolymer, a urethane and silicone.

27. The transdermal delivery system according to claim 16, wherein the softening agent is at least one of dodecanol, undecanol, octanol, a glycol and glycanol.

28. The transdermal delivery system according to claim 16, wherein the solvent is a monoester of a dicarboxylic acid.

29. The transdermal delivery system according to claim 16, wherein the solvent is at least one of monomethyl glutarate and monomethyl adipate.

30. The transdermal delivery system according to claim 16, wherein by weight the polymer is present in about 55%, the felodipine in about 10%, the solvent in about 10% and the softener in about 15%.

31. A transdermal delivery system according to claim 16, wherein the solvent is present in from about 25 to 100% the weight of the felodipine.

32. The transdermal delivery system according to claim 16, which also comprises a removable protective layer.

33. The transdermal delivery system according to claim 16, wherein the pressure-sensitive adhesive reservoir layer comprises a polymer based on an acrylate, a methacrylate, a silicon compound or a combination thereof.

34. The transdermal delivery system according to claim 16, wherein the softening ester is a medium-chain triglyceride of the caprylic/capric acids of coconut oil.

35. The transdermal delivery system according to claim 16, wherein the solvent has at least one acidic group.

36. The method of claim 1, wherein said transdermal delivery system has a mean relative release rate of felodipine of from about 2.9 µg/cm²/hr to about 7.9 µg/cm²/hr at 120 hours;

from about 3.2 µg/cm²/hr to about 7.9 µg/cm²/hr at 144 hours;

and from about 3.0 µg/cm²/hr to about 7.9 µg/cm²/hr at 168 hours; as determined via an in-vitro permeation test utilizing a Valia-Chien cell where the membrane is a human cadaver skin, said cell having a receptor chamber containing a 40:60 mixture of ethanol:water.

37. The transdermal delivery system of claim 14, wherein said transdermal delivery system has a mean relative release rate of felodipine of from about 2.9 µg/cm²/hr to about 7.9 µg/cm²/hr at 120 hours;

from about 3.2 µg/cm²/hr to about 7.9 µg/cm²/hr at 144 hours;

and from about 3.0 µg/cm²/hr to about 7.9 µg/cm²/hr at 168 hours; as determined via an in-vitro permeation test utilizing a Valia-Chien cell where the membrane is a human cadaver skin, said cell having a receptor chamber containing a 40:60 mixture of ethanol:water.

* * * * *